United States Patent
Park et al.

(10) Patent No.: US 10,251,040 B2
(45) Date of Patent: Apr. 2, 2019

(54) HOTEL SERVICE PROVIDING METHOD AND HOTEL SERVICE PROVIDING SYSTEM

(71) Applicant: Samsung Electronics Co., Ltd., Gyeonggi-do (KR)

(72) Inventors: Hyun Mi Park, Seoul (KR); Do Hyoung Kim, Seoul (KR); Tae Youn Kim, Gyeonggi-do (KR); Hee Seon So, Seoul (KR); Ka Won Cheon, Seoul (KR)

(73) Assignee: Samsung Electronics Co., Ltd (KR)

( * ) Notice: Subject to any disclaimer, the term of this patent is extended or adjusted under 35 U.S.C. 154(b) by 0 days.

(21) Appl. No.: 15/419,578

(22) Filed: Jan. 30, 2017

(65) Prior Publication Data
US 2017/0223482 A1    Aug. 3, 2017

(30) Foreign Application Priority Data

Jan. 29, 2016   (KR) .................. 10-2016-0011134

(51) Int. Cl.
*H04B 7/00*    (2006.01)
*H04W 4/80*   (2018.01)
(Continued)

(52) U.S. Cl.
CPC ............... *H04W 4/80* (2018.02); *A61B 5/002* (2013.01); *A61B 5/4809* (2013.01);
(Continued)

(58) Field of Classification Search
CPC ........ A61B 2503/12; A61B 2562/0247; A61B 5/002; A61B 5/4809; A61B 5/4815;
(Continued)

(56) References Cited

U.S. PATENT DOCUMENTS 8,301,270 B2   10/2012   Quail
8,825,118 B2   9/2014   Kim et al.
(Continued)

FOREIGN PATENT DOCUMENTS

GB    2 490 961    11/2012
KR    20070082256    8/2007
(Continued)

OTHER PUBLICATIONS

International Search Report dated Jul. 5, 2017 issued in counterpart application No. PCT/KR2017/000999, 13 pages.
(Continued)

*Primary Examiner* — Xin Jia
(74) *Attorney, Agent, or Firm* — The Farrell Law Firm, P.C.

(57) ABSTRACT

An electronic device is provided. The electronic device includes a housing, a communication circuit configured to perform short range communication with a mobile device by using a first communication channel and perform wireless communication with an external output device by using a second communication channel and a control circuit configured to, when the mobile device is located on or in close proximity to the housing, obtain content that is being output by the mobile device through the first communication channel and transmit the obtained content to the external output device through the second communication channel.

11 Claims, 16 Drawing Sheets

(51) Int. Cl.
*A61B 5/00* (2006.01)
*G01L 5/00* (2006.01)
*G06Q 50/12* (2012.01)
*H02J 7/02* (2016.01)
*H04W 76/30* (2018.01)
*H02J 7/00* (2006.01)

(52) U.S. Cl.
CPC .......... *A61B 5/4815* (2013.01); *A61B 5/6892* (2013.01); *A61B 5/742* (2013.01); *G01L 5/0028* (2013.01); *G06Q 50/12* (2013.01); *H02J 7/025* (2013.01); *A61B 2503/12* (2013.01); *A61B 2560/0219* (2013.01); *A61B 2562/0247* (2013.01); *H02J 2007/0096* (2013.01); *H04W 76/30* (2018.02)

(58) Field of Classification Search
CPC ..... A61B 5/6892; A61B 5/742; G01L 5/0028; G06Q 50/12; H02J 7/025; H04W 4/008; H04W 4/80; H04W 76/06; H04W 76/30
See application file for complete search history.

(56) References Cited

U.S. PATENT DOCUMENTS

| | | | |
|---|---|---|---|
| 9,158,292 | B2 | 10/2015 | Quail |
| 9,294,899 | B2 | 3/2016 | Lee |
| 9,729,211 | B2 | 8/2017 | Gomes-Casseres et al. |
| 2010/0191352 | A1 | 7/2010 | Quail |
| 2012/0115549 | A1 | 5/2012 | Kim et al. |
| 2013/0027289 | A1* | 1/2013 | Choi .................. G06F 3/14 345/156 |
| 2013/0090746 | A1 | 4/2013 | Quail |
| 2013/0267168 | A1* | 10/2013 | Jeon .................. H04B 5/0025 455/41.1 |
| 2014/0087686 | A1 | 3/2014 | Lee |
| 2014/0140530 | A1 | 5/2014 | Gomes-Casseres et al. |
| 2014/0295758 | A1 | 10/2014 | Pedersen |
| 2014/0370810 | A1* | 12/2014 | Huang .................. H04B 7/26 455/41.2 |
| 2015/0195860 | A1 | 7/2015 | Joshi |
| 2016/0183056 | A1* | 6/2016 | Leabman .............. H04W 4/025 455/456.3 |
| 2017/0018248 | A1 | 1/2017 | Na |

FOREIGN PATENT DOCUMENTS

| | | |
|---|---|---|
| KR | 1020100086777 | 8/2010 |
| KR | 20130066896 | 6/2013 |
| KR | 1020140006613 | 1/2014 |
| KR | 20140099769 | 8/2014 |
| KR | 1020140146414 | 12/2014 |
| KR | 20150098098 | 8/2015 |
| KR | 1020150103927 | 9/2015 |
| WO | WO 2012/079619 | 6/2012 |

OTHER PUBLICATIONS

European Search Report dated Nov. 19, 2018 issued in counterpart application No. 17744615.0-1213, 12 pages.

* cited by examiner

HOTEL SERVICE PROVIDING METHOD AND HOTEL SERVICE PROVIDING SYSTEM

PRIORITY

This application claims priority under 35 U.S.C. § 119(a) to Korean Patent Application Serial No. 10-2016-0011134, which was filed on Jan. 29, 2016 in the Korean Intellectual Property Office, the entire disclosure of which is incorporated herein by reference.

BACKGROUND

1. Field of the Disclosure

The present disclosure relates generally to an electronic device, and more particularly, to an electronic device that is configured to communicate with a hotel communication system, which may provide various services for a user of the electronic device.

2. Description of the Related Art

Hotels provide various services to their guests. For example, hotels provide various localized services or hotel-specific services, as well as amenities, such as a swimming pool, transportation service, a bar or a restaurant. Further, the rooms for guests of the hotel are provided with a plurality of light bulbs, various pieces of equipment, TV, mini-bar, iron and ironing board, shower, desk, wired or wireless internet connection, etc.

However, most hotels fail to provide adequate information relating to services provided outside the hotels to the guests, such as information relating to surrounding scenes, affiliate events, etc. For example, the guests may refer to information magazines in the form of booklets placed in the rooms, or signs placed in hotel lobbies to recognize the various programs or services provided by outside entities other than the hotels, but it is often very inefficient, e.g., such booklets can sometimes be out dated.

SUMMARY

Aspects of the present disclosure have been made to address at least the above-mentioned problems and/or disadvantages and to provide at least the advantages described below. Accordingly, an aspect of the present disclosure is to provide a method and a system for constructing a service environment between a user device and a hotel network to provide various pieces of information through an electronic device placed in a room or the user device based on a user schedule or a user preference.

In accordance with an aspect of the present disclosure, there is provided an electronic device. The electronic device includes a communication circuit configured to perform short range communication with a mobile device by using a first communication channel and perform wireless communication with an external output device by using a second communication channel and a control circuit configured to, when the mobile device is located on or in close proximity to the electronic device, obtain content that is being output by the mobile device through the first communication channel and transmit the obtained content to the external output device through the second communication channel.

In accordance with an aspect of the present disclosure, there is provided an electronic device. The electronic device includes a communication circuit and a control circuit configured to: obtain, from a central system, a hotel schedule comprising a plurality of programs and information of a user registered in the central system; obtain from the mobile device, a schedule of the user registered in a mobile device of the user; and provide a program of the plurality of programs with respect to a time slot, in which a schedule of the user is not set, based on the hotel schedule and the user information.

In accordance with an aspect of the present disclosure, there is provided an electronic device. The electronic device includes a communication circuit in operable communication with a sensor attached to one of a bed, a lighting device, an audio output device, and a video output device and a control circuit in operable communication with the communication circuit and configured to determine a state associated with a sleep of a user based at least on a value obtained by the sensor, and to transmit a predefined control command to one of the lighting device, the audio output device, and the video output device based on the determined state.

BRIEF DESCRIPTION OF THE DRAWINGS

The above and other aspects, features, and advantages of certain embodiments of the present disclosure will be more apparent from the following detailed description taken in conjunction with the accompanying drawings, in which.

DETAILED DESCRIPTION

Figure 1:
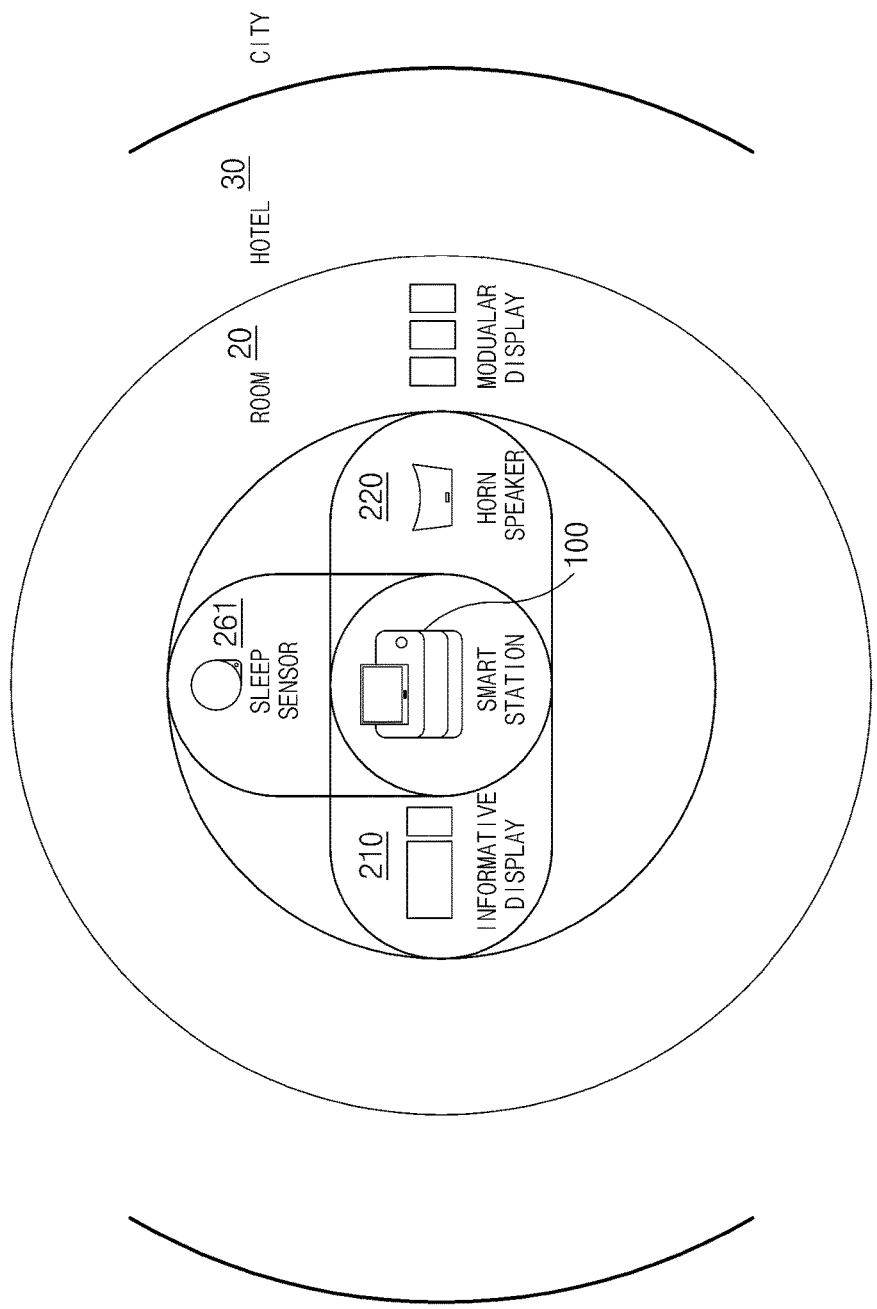
FIG. 1 is a diagram of a room service provided by a hotel, according to an embodiment of the present disclosure.

Embodiments of the present disclosure will be described herein below with reference to the accompanying drawings. However, the embodiments of the present disclosure are not limited to the specific embodiments and should be construed as including all modifications, changes, equivalent devices and methods, and/or alternative embodiments of the present disclosure.

The terms "have," "may have," "include," and "may include" as used herein indicate the presence of corresponding features (for example, elements such as numerical values, functions, operations, or parts), and do not preclude the presence of additional features.

The terms "A or B," "at least one of A or/and B," or "one or more of A or/and B" as used herein include all possible combinations of items enumerated with them. For example, "A or B," "at least one of A and B," or "at least one of A or B" means (1) including at least one A, (2) including at least one B, or (3) including both at least one A and at least one B.

The terms such as "first" and "second" as used herein may modify various elements regardless of an order and/or importance of the corresponding elements, and do not limit the corresponding elements. These terms may be used for the purpose of distinguishing one element from another element. For example, a first user device and a second user device may indicate different user devices regardless of the order or importance. For example, a first element may be referred to as a second element without departing from the scope the present invention, and similarly, a second element may be referred to as a first element.

It will be understood that, when an element (for example, a first element) is "(operatively or communicatively) coupled with/to" or "connected to" another element (for example, a second element), the element may be directly coupled with/to another element, and there may be an intervening element (for example, a third element) between the element and another element. To the contrary, it will be understood that, when an element (for example, a first element) is "directly coupled with/to" or "directly connected to" another element (for example, a second element), there is no intervening element (for example, a third element) between the element and another element.

The expression "configured to (or set to)" as used herein may be used interchangeably with "suitable for," "having the capacity to," "designed to," "adapted to," "made to," or "capable of" according to a context. The term "configured to (set to)" does not necessarily mean "specifically designed to" in a hardware level. Instead, the expression "apparatus configured to . . . " may mean that the apparatus is "capable of . . . " along with other devices or parts in a certain context. For example, "a processor configured to (set to) perform A, B, and C" may mean a dedicated processor (e.g., an embedded processor) for performing a corresponding operation, or a generic-purpose processor (e.g., a CPU or an application processor) capable of performing a corresponding operation by executing one or more software programs stored in a memory device.

The term "module" as used herein may be defined as, for example, a unit including one of hardware, software, and firmware or two or more combinations thereof. The term "module" may be interchangeably used with, for example, the terms "unit", "logic", "logical block", "component", or "circuit", and the like. The "module" may be a minimum unit of an integrated component or a part thereof. The "module" may be a minimum unit performing one or more functions or a part thereof. The "module" may be mechanically or electronically implemented. For example, the "module" may include at least one of an application-specific integrated circuit (ASIC) chip, field-programmable gate arrays (FPGAs), or a programmable-logic device, which is well known or will be developed in the future, for performing certain operations.

The terms used in describing the various embodiments of the present disclosure are for the purpose of describing particular embodiments and are not intended to limit the present disclosure. As used herein, the singular forms are intended to include the plural forms as well, unless the context clearly indicates otherwise. All of the terms used herein including technical or scientific terms have the same meanings as those generally understood by an ordinary skilled person in the related art unless they are defined otherwise. The terms defined in a generally used dictionary should be interpreted as having the same or similar meanings as the contextual meanings of the relevant technology and should not be interpreted as having ideal or exaggerated meanings unless they are clearly defined herein. According to circumstances, even the terms defined in this disclosure should not be interpreted as excluding the embodiments of the present disclosure.

Hereinafter, a hotel service, a device, and a system for providing the hotel service will be described with reference to the accompanying drawings. Although the present disclosure provides a description of a hotel and a service provided in a room of the hotel, the present disclosure is not so limited, and the present disclosure could also be used in other environments, such as a resort, a first class seat of an airplane, or a business center.

FIG. 1 is a diagram of a room service provided by a hotel, according to an embodiment of the present disclosure.

Referring to FIG. 1, a hotel 30 may have a plurality of rooms 20, and a control smart station 100 (smart station 100) may be placed in each of the rooms 20 of the hotel 30. The smart station 100 may be understood as a control station that communicates with a user device 240 (FIG. 2) and controls electronic devices placed in the room. The electronic device placed in the room may be simply referred to as an in-room device.

Figure 2:
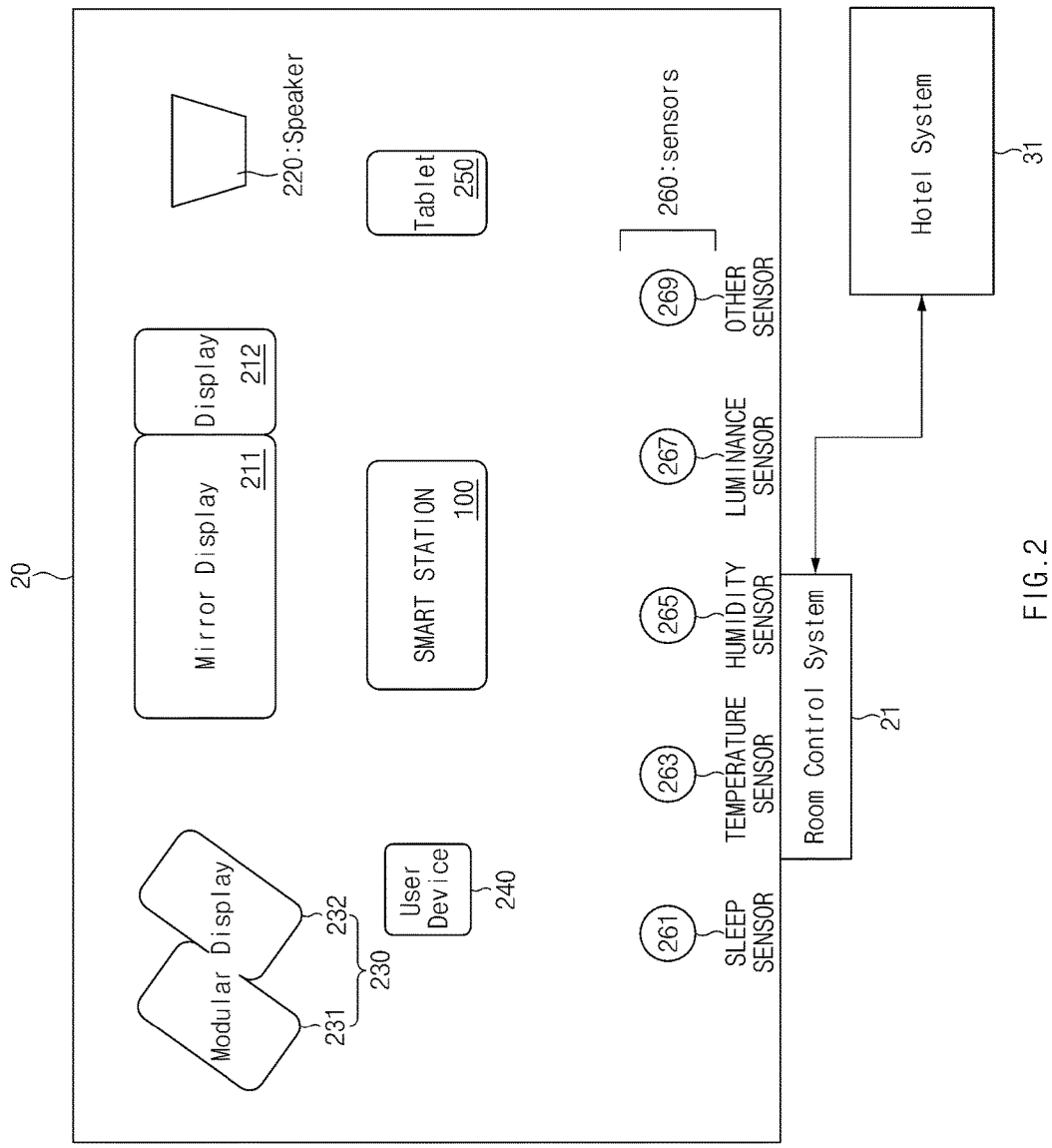
FIG. 2 is a diagram of an environment of a hotel system, a room system, and a user device, according to an embodiment of the present disclosure.

The smart station 100 may function as a network hub between any two of the user devices 240, the in-room devices, and a room control system 21 (FIG. 2). Further, the smart station 100 may directly control some of the in-room devices through transmission of a control message/signal.

An informative mirror display 210 may have an attribute of a mirror. The informative mirror display 210 may display contents and/or information based on a context. The informative mirror display 210 may be operated as a mirror TV. For example, if a user turns on a TV by using a remote controller or the like, the informative mirror display 210 may output a broadcast program of a specific channel on a screen of the TV. If the TV function is turned off, the informative mirror display 210 may reflect peripheral light like a mirror.

The informative mirror display 210 may be implemented by coupling one mirror display device or a plurality of informative mirror display devices to one or more other display devices. In the following description, it may be understood that "a display" refers to devices that constitute an informative mirror display 210 or devices that constitute a modular display 230 (FIG. 2), which will be described in greater detail below. When any one display device of a plurality of display devices is included in one display, it will be referred to as "a display device". For example, the informative mirror display 210 may include one informative mirror display device 211 and a modular display device 212 (FIG. 2). In this instance, only the informative mirror display device 211 may have the characteristics of a mirror.

If the informative mirror display device 211 does not utilize the characteristics of the informative mirror display 210, the informative mirror display 210 may be replaced, simply, by a conventional display, a conventional TV, or the modular display device 212.

A horn speaker 220 may correspond to an example of an audio output device having a horn shape. The horn speaker 220 may be arranged at a suitable location based on the structure of a room to maximize the effect of the horn speaker 220. The horn speaker 220 is an example of an audio output device, and may be more generally referred as a speaker 220. Further, the speaker 220 may refer to one or more audio output devices.

A sleep sensor 261 may be a sensor for determining whether a user is sleeping. The sleep sensor 261 may be a sensor that does not directly determine whether or not the user is sleeping but determines whether there is a high possibility of a surrounding context corresponding to a context in which the user is about to sleep. For example, the sleep sensor 261 may be attached to a lower part or the interior of a bed to measure a force that is applied to the bed and determine whether the user is laying or seated on the bed or if there is no one on the bed based on a measured force value. The sleep sensor 261 may correspond to a pressure detecting sensor. The sleep sensor 261 may simply transmit a measured value to the smart station 100, and the smart station 100 may determine whether the user is currently sleeping or preparing for sleep by collectively considering a current time, a current intensity of illumination in the room 20, whether the informative mirror display 210 is currently outputting a TV broadcast program, and/or a schedule of the user.

The smart station 100 may monitor operation environments of a plurality of in-room devices, such as the informative mirror display 210, the horn speaker 220, and the sleep sensor 261, and may provide a smart station based service environment 10 based on the monitoring result.

The smart station based service environment 10 may be associated with a room 20 service environment and/or a hotel 30 service environment. For example, the smart station 10 may transmit information that the user is currently preparing for sleep, based on the information obtained by the sleep sensor 261. The room control system 21 may control the devices of the room, which are not controlled by the smart station 100, to provide a comfortable sleep environment for the user. For example, the room control system 21 may turn off the modular display 230 or control a ventilation system, a cooling/heating system, a sleep state monitoring system, or the like for a suitable sleep environment.

When the user checks into a hotel, the information of the user may be registered in a hotel system 31 (FIG. 2). The hotel system 31 is a central control system of the hotel, and may control the entire environment (e.g., temperature, humidity, air, and lighting) of the hotel 30 and the room control systems 21 of the rooms 20 of the hotel 30. The hotel system 31 may transmit information on a name, a sex, and a stay schedule, and the like to the room control system 21. The room control system 21 may transmit user information to the smart station 100 if it is detected that a door of the room 20 is opened, and the smart station 100 may control the informative mirror display 210 such that a welcome message is output, thereby increasing the satisfaction of the user. For example, if the user is a female named Alice, as in context 310 of FIG. 3, a message of "WELCOME! Ms. Alice" may be output on the informative mirror display 210.

The operations that have been described to be performed by any one of the smart station 100, the room control system 21, and the hotel system 31 may be performed by the other devices. For example, the room control system 21 may directly control the informative mirror display 210 and not through the smart station 100.

FIG. 2 is a diagram of a hotel system, a room system, and a user device, according to an embodiment of the present disclosure.

Referring to FIG. 2, a room 20 service environment may include the smart station 100, the informative mirror display 210, the speaker 220, the modular display 230, a user device 240, a tablet 250 that is placed in the room 20 to be associated with the room 20, and various sensors 260. Here, the other devices, except for the user device 240, may be placed in the room 20 in advance.

The sensors 260 may include the sleep sensor 261, a temperature sensor 263, a humidity sensor 265, a luminance sensor 267, and one or more other sensors 269. For example, the other sensors 269 may include a room door opening/closing detecting sensor, an infrared ray sensor, and a heat detecting sensor. The sensors 260 may measure a physical property or sense an operating state of the electronic device 201, and may convert the measured or sensed information into an electric signal. The sensors 260 may further include a control circuit for controlling one or more sensors included therein.

The smart station 100 corresponds to the smart station 100 of FIG. 1. An example of an external shape of the smart station 100 will be described in greater detail with reference to FIG. 5, and an example of an internal configuration of the smart station 100 will be described in greater detail with reference to FIG. 6.

The informative mirror display 210 may be implemented by the informative mirror display device 211 and one or more display devices 212 that are connected with the informative mirror display device 211. However, the informative mirror display 210 may be the informative mirror display device 211 itself. An example of a connection structure of the informative mirror display 210 will be described in greater detail with reference to FIG. 3.

The speaker 220 may correspond to the horn speaker 220, but may correspond to other general speakers. The speaker 220 may output an audio signal that is generated by the smart station 100, the user device 240, the room control system 21, and/or the hotel system 31. However, when the smart station 100 or the informative mirror display 210 supports an audio output function, the speaker 220 may be excluded. A description that the room control system 21 turns off an audio output of the room 20 may be defined as the room control system 21 turning off a power supply of the speaker 220 or adjusting a volume of the speaker from 10 to 0, either directly or indirectly through the smart station 100.

The modular display 230 may be implemented through coupling of contact points of a first display device 231 and a second display device 232. For example, the first display device 231 and the second display device 232 may contact each other while portions of side surfaces thereof are shared. The sizes, the resolutions, the models, and the like of the first display device 231 and the second display device 232 may be the same. However, the first display device 231 and the second display device 232 may be different devices.

For example, the first display device 231 and the second display device 232 may each have at least one contact point structure on a side surface thereof. The contact point structures of the different devices may be connected with each other physically and by circuitry. For example, the contact structures may be physically connected with each other by the magnets provided in the contact structures, and data ports and/or power ports, which are suitably arranged in the contact structures, may be connected with each other through the physical connections or by circuitry.

The first display device 231 or the second display device 232 may be operated as a master device and the other one may be operated as a passive (or slave) device. For example, when the first display device 231 is operated as a master display device, it may determine a first area, which will be output by the first display device 231, a second area, which will be output by the second display device 232, and form content, which will be output, based on arrangement of the modular display 230. The first display device 231 may output data corresponding to the first area on a display panel of the first display device 231, and may transmit output data corresponding to the second area to the second display device 232. The second display device 232 may output data corresponding to the second area on a display panel thereof.

When the arrangement (e.g., an inclination or a location of a contact point) of the modular display 230 is changed, the second display device 232 can be separated or a third display device can be additionally connected, and the first display device 231 can be operated as a master display device and may change output areas of contents, which will be output from the display devices based on the changed arrangement of the modular display 230. When the first display device 231 is separated from the modular display 230, any one (e.g., the second display device 232) of the display devices that have functioned as passive devices may function as a master display device, and the other display devices that constitute the modular display 130 may be operated as passive devices.

The user device 240 may be registered in the hotel system 31 when the user checks into the hotel. For example, when the user registers the user device 240 while checking into a room at the front desk of the hotel, information related to the user device 240 together with the user information may be stored in the hotel system 31. For example, in addition to the name, the sex, and the stay period of the user, information of the user device 240, such as the phone number and the unique identification number (e.g., a serial number of the product) of the user device 240, the model name of the user device 240, and a schedule of the user stored in the user device 240 may be stored. In this instance, authentication information or an access authority that is necessary when the user device 240 uses a network, such as wireless fidelity (Wi-Fi), near field communication (NFC), or Bluetooth (BT), in a room or a lobby of the hotel may be set in the hotel system 31 or the user device 240 in advance. Accordingly, the user may conveniently use a hotel service without asking for a Wi-Fi password, or may conveniently use a hotel 30 service without having to request permission.

Further, an application (e.g., a dedicated application of the hotel) that is associated with the hotel 30 may be installed in the user device 240. Information registered in the application associated with the hotel 30 or information registered during a stay period may be delivered to the hotel system 31. For example, information on the number of stays in a corresponding hotel, other hotels of the same brand, or affiliate hotels, food preferences or preferred activities (e.g., swimming, massage, golf, a touring destination, and the like) of the user may be delivered to the hotel system 31.

The tablet 250 may be placed in a room and may constitute a part of the room 20 service environment. The tablet 250 may provide various information related to the room 20.

Some of the various in-room devices that constitute the room 20 service environment may be electrically connected with the room control system 21, or may be controlled through wireless communication. For example, the room control system 21 may transmit a control command to the smart station 100 or the speaker 220 through a wireless network. Further, the room control system 21 may synchronize information that may be provided by the tablet 250 with data of the hotel system 31 by using a wireless network.

The room control system 21 may control other in-room devices through wired network communication. For example, at least some of the informative mirror display 210, the modular display 230, or the sensors 260 may be arranged on a wall surface of the room 20, or may be connected with the room control system 21 through a wiring structure of the wall surface. The room control system 21 may supply electric power to the informative mirror display 310 or the modular display 230 and may provide data that will be output.

The room 20 service environment may further include other components, which are not illustrated. For example, a lighting device, a cooling or heating device, a hot water system, and a ventilation system of the room may be included in the room 20 service environment, and may be controlled by the smart station 100 or the room control system 21.

Figure 3:
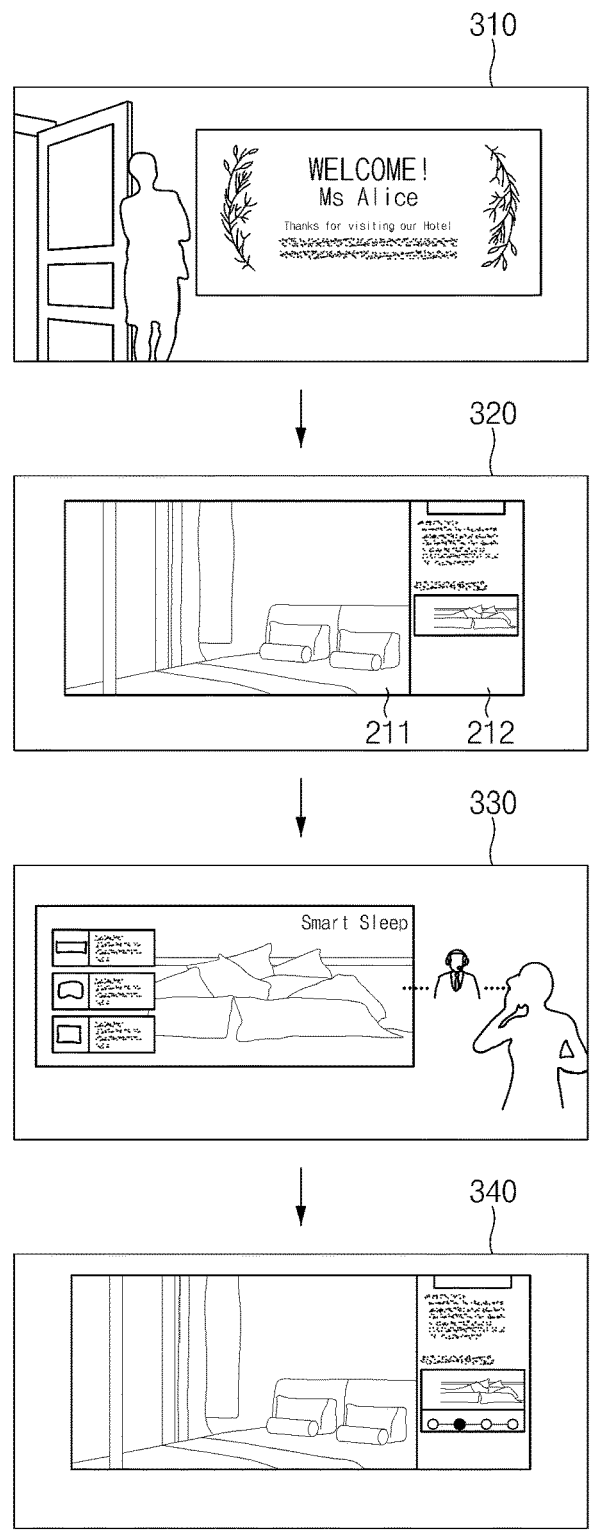
FIG. 3 is a diagram illustrating a manner in which a user uses a room, according to an embodiment of the present disclosure.

FIG. 3 is a diagram illustrating a way in which a user uses a room, according to an embodiment of the present disclosure.

Regarding reference number 310, the user may enter the room 20 first, after checking into the hotel 30. The room control system 21 may receive information of the user who has checked into the hotel 30 from the hotel system 31. The room control system 21 may determine the name of the user (e.g., Alice) who is scheduled to stay in the room and whether the user enters the room for the first time (e.g., the number of openings of the room door is 0 after checking into the hotel). If the door of the room is opened, that is, if the number of openings of the room door is changed from 0 to 1 after the user checks into the room, the room control system 21 may control the informative mirror display 210 such that a welcome message (e.g., WELCOME! Ms. Alice) may be output on the informative mirror display 210.

Regarding reference number 320, if it is identified that the user has entered the room 20, the room control system 21 may display an introduction of the services, which may be provided by the hotel 30, on the informative mirror display 210. For example, information of a smart sleep service that guides a comfortable sleep of the user may be provided. In this instance, the welcome message disappears, the informative mirror display device 211 of the informative mirror display 210 may be operated as a mirror, and an introduction content on the service may be displayed only on the display device 212 coupled to the informative mirror display device 211.

The room control system 21 may identify whether the user has entered the room 20 through various methods. For example, when a network connection, such as BT or Wi-Fi, is established between the smart station 100 and the user device 240, through tracking of the user device 240, or through a room entrance identifying event by using an application of the user device 240, the room control system 21 may identify whether the user has entered the room.

Regarding reference number 330, the user may inquire detailed information on the smart sleep from a hotel clerk, through a phone call or the like. If the hotel clerk controls the hotel system 31 to provide information on the smart sleep, a screen based on the control result may be output on the informative mirror display 210. For example, if the hotel clerk selects a room number of the user from the hotel system 31 (or a PC connected with the hotel system 31) and executes an image or video related to a service, which is to be described by him or her, the hotel system 31 controls the room control system 21 such that the corresponding image or video may be output on the informative mirror display 210. Because the user watches a screen related to the explanation of the hotel clerk at the same time, he or she may obtain a high understanding of the service and may be very satisfied with the room environment.

Regarding reference number 340, the user may apply for a service provided by the hotel 30. For example, regarding reference number 330, the user may apply a smart sleep service immediately after listening to the explanation about the smart sleep. The processes of receiving, processing, and apply the application by the hotel system 31 may be output on the informative mirror display 210 stage by stage. Accordingly, the user may easily recognize how the service applied by him or her is processed. For example, when the user apply for a wine party program, he or she may easily recognize whether his or her participation was approved, in a standby state, or rejected.

Figure 4:
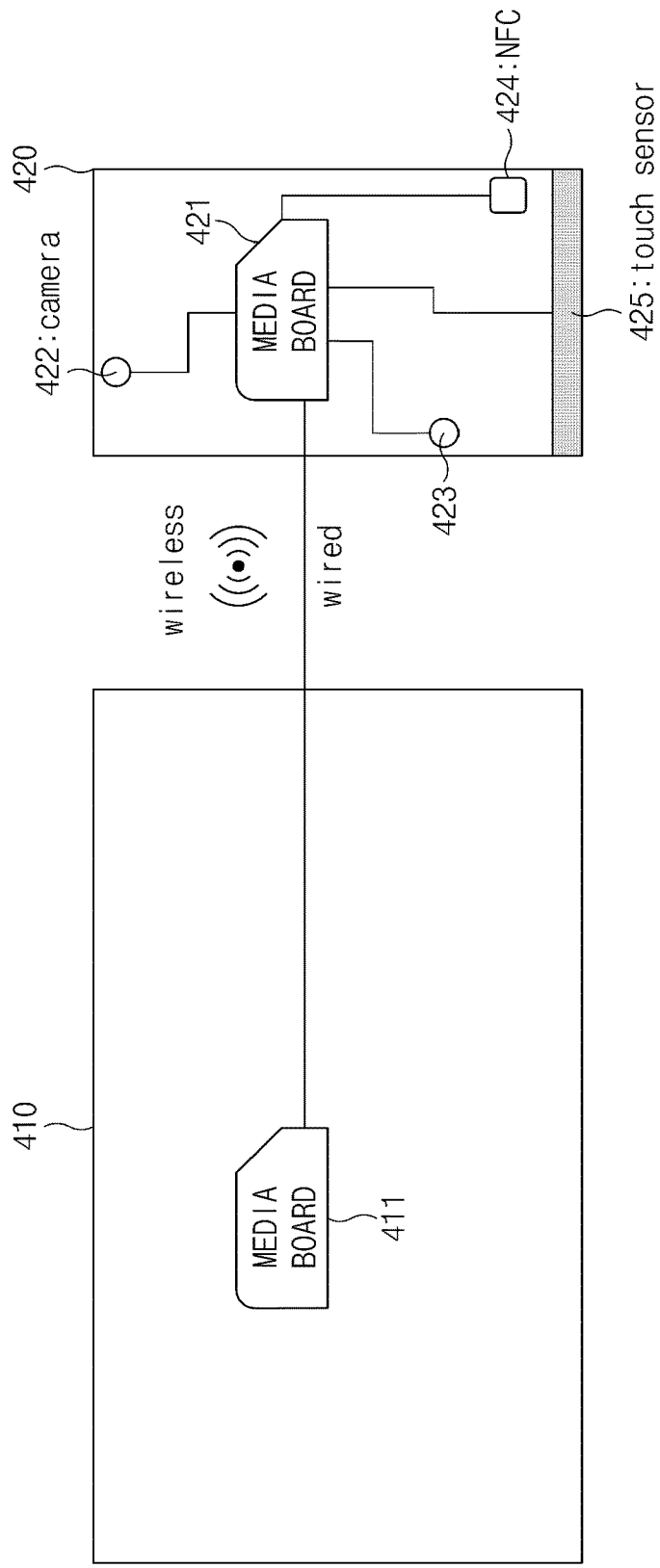
FIG. 4 is a diagram of a connection structure of an informative mirror display, according to an embodiment of the present disclosure.

FIG. 4 is a diagram of an informative mirror display, according to an embodiment of the present disclosure.

Referring to FIG. 4, the display device 410 may correspond to the informative mirror display device 211. Further, the display device 420 may correspond to the display device 212.

The display device 410 may include a display panel, and glass that both transmits and reflects light. For example, if a TV screen is output through the display panel, the glass transmits the TV screen (internal light) such that the user may watch the TV screen, but in a state in which the display panel is off, the glass may reflect external light to be operated as a mirror.

The display device 420 may include a mirror function. The display device 420 may correspond to the first display device 231 that constitutes the above-described modular display 230. The display device 410 and the display device 420 may transmit and receive data to and from each other through a wired network interface connected with the display device 410 and the display device 420 through a contact structure, for example, similarly to the modular display 230. The wired communication may include, for example, at least one of a universal serial bus (USB), USB type-C (USB-C), a high definition multimedia interface (HDMI), recommended standard-232 (RS-232), and inter-integrated circuit (I2C). The display device 410 and the display device 420 may transmit and receive data through a wireless network.

For example, content is output on an entire screen of the informative mirror display including the display device 410 and the display device 420 and a media board 421 of the display device 420 may determine areas, in which the content is to be output, of the display device 410 and the display device 420 and may transmit data on the determined areas to the display device 410 through a wired or wireless network. The media board 411 of the display device 410 may output the transmitted data to the display panel. Here, the media boards 411 and 421 may correspond to a control circuit.

The display device 420 may include other additional functions. For example, the display device 420 may include a camera module 422, a proximity sensor 423, an NFC circuit 424, and/or a touch sensor 425.

An image captured by the camera module 422 may be output on the display device 410, or may be transmitted to the user device 240 through the smart station 100. If the proximity sensor 423 recognizes that the user is near the display device 420, an information screen on suitable services may be provided. Further, when the user device 240 supports an NFC function, the NFC circuit 424 may provide a function of providing information or registering a program through NFC tagging. Further, the user may perform a touch input to the display device 420 through the touch sensor 425.

Figure 5:
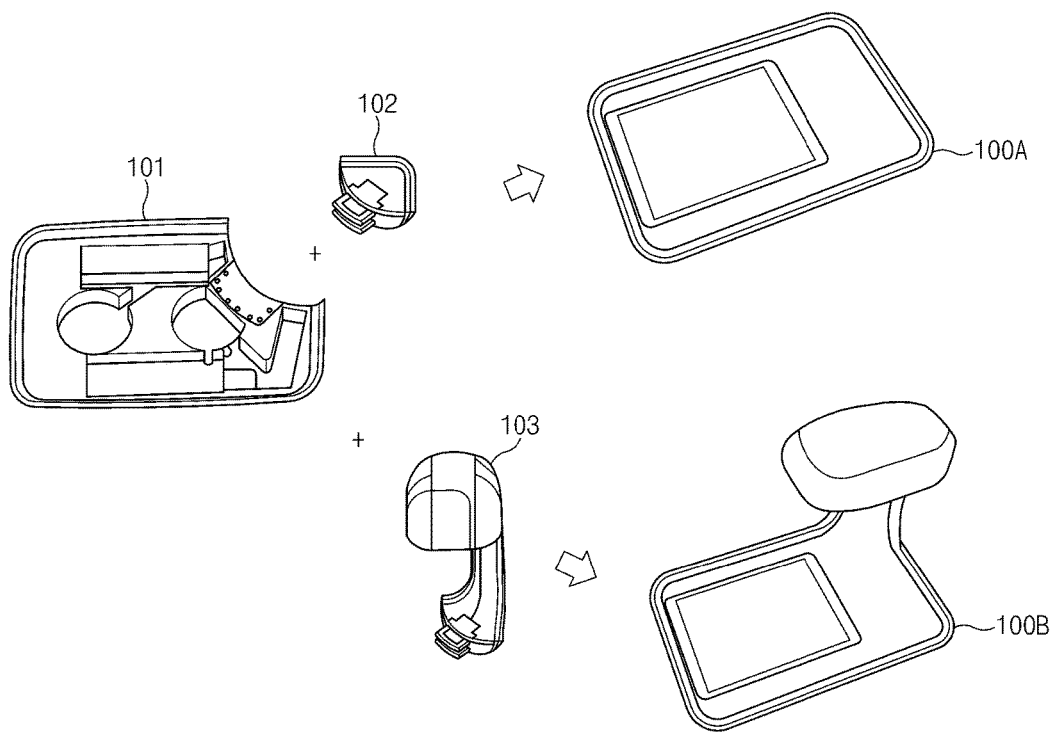
FIG. 5 is a diagram of an external shape and a coupling structure of a control station, according to an embodiment of the present disclosure.

FIG. 5 is a diagram of an external shape and a coupling structure of a smart station, according to an embodiment of the present disclosure.

Referring to FIG. 5, the smart station 100 may be implemented through coupling of a main body 101 and sub-bodies 102 and 103. For example, the smart station 100 may have a first shape 100A through coupling of the main body 101 and a first sub-body 102. In another example, the smart station 100 may have a second shape 100B through coupling of the main body 101 and a second sub-body 103.

The first sub-body 102 and the second sub-body 103 may be connected with the main body 101 mechanically and by circuitry. The first sub-body 102 and the second sub-body 103 support some functions in common, but may support different specific functions, respectively. For example, the second sub-body 103 may further include a function of a network relay, a function of a speaker, and a state display function using light emitting diode (LED), in addition to a function supported by the first sub-body 102.

The smart station 100 may include a planar surface on at least a portion of an outer housing of the smart station 100. If a mobile device such as a user device 240 or a tablet 250 is located on the planar surface of the smart station 100, the smart station 100 may perform wireless charging by using a wireless charging coil arranged under the planar surface or may perform a media plugging function, which will be described in greater detail with reference to FIG. 7.

Figure 6:
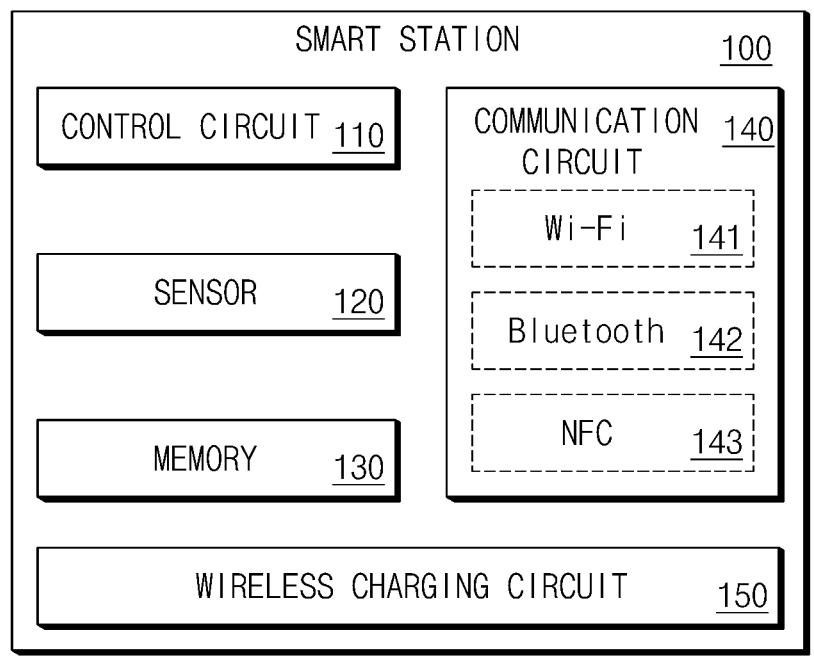
FIG. 6 is a diagram of a control station, according to an embodiment of the present disclosure.

FIG. 6 is a diagram of hardware that constitutes a smart station, according to an embodiment of the present disclosure.

Referring to FIG. 6, the smart station 100 includes a control circuit 110, a sensor 120, a memory 130, a communication circuit 140, and a wireless charging circuit 150. At least one of the components of the smart station 100 may be excluded or another component may be additionally included.

The processor 110 may include one or more of a central processing unit (CPU), an application processor (AP), or a communication processor (CP). The control circuit 110 may execute operations or data processing related to the control and/or communication of at least one other component of the smart station 100.

The sensor 120 may include at least one of the sensors 260, which have been described as the in-room devices. The sensor 120 may correspond to a pressure sensor or a proximity sensor for detecting whether the mobile device is positioned on the planar surface of the housing of the smart station 100.

The memory 130 may include volatile and/or nonvolatile memories. The memory 130 may store a command or data related to at least one other component of the smart station 100. Further, the memory 130 may permanently or temporarily store data provided by the room control system 21, the user device 240, or the in-room devices.

The communication circuit 140 may set communication between the smart station 100 and the user device 240, the informative mirror display 210, or the speaker 220. For example, the communication circuit 140 may communicate with an external device through wireless communication.

The wireless communication may include a short range communication. The short range communication 164 may include at least one of Wi-Fi, BT, NFC, Wi-Fi Direct, or BT low energy (BLE).

The wireless charging circuit 150 may include at least one circuit for implementing wireless charging, such as a magnetic resonance type, a magnetically inductive type, or an electromagnetic wave type. To this end, the wireless charging circuit may further include an additional circuit for wireless charging, a coil loop, a resonance circuit, or a rectifier.

Figure 7:
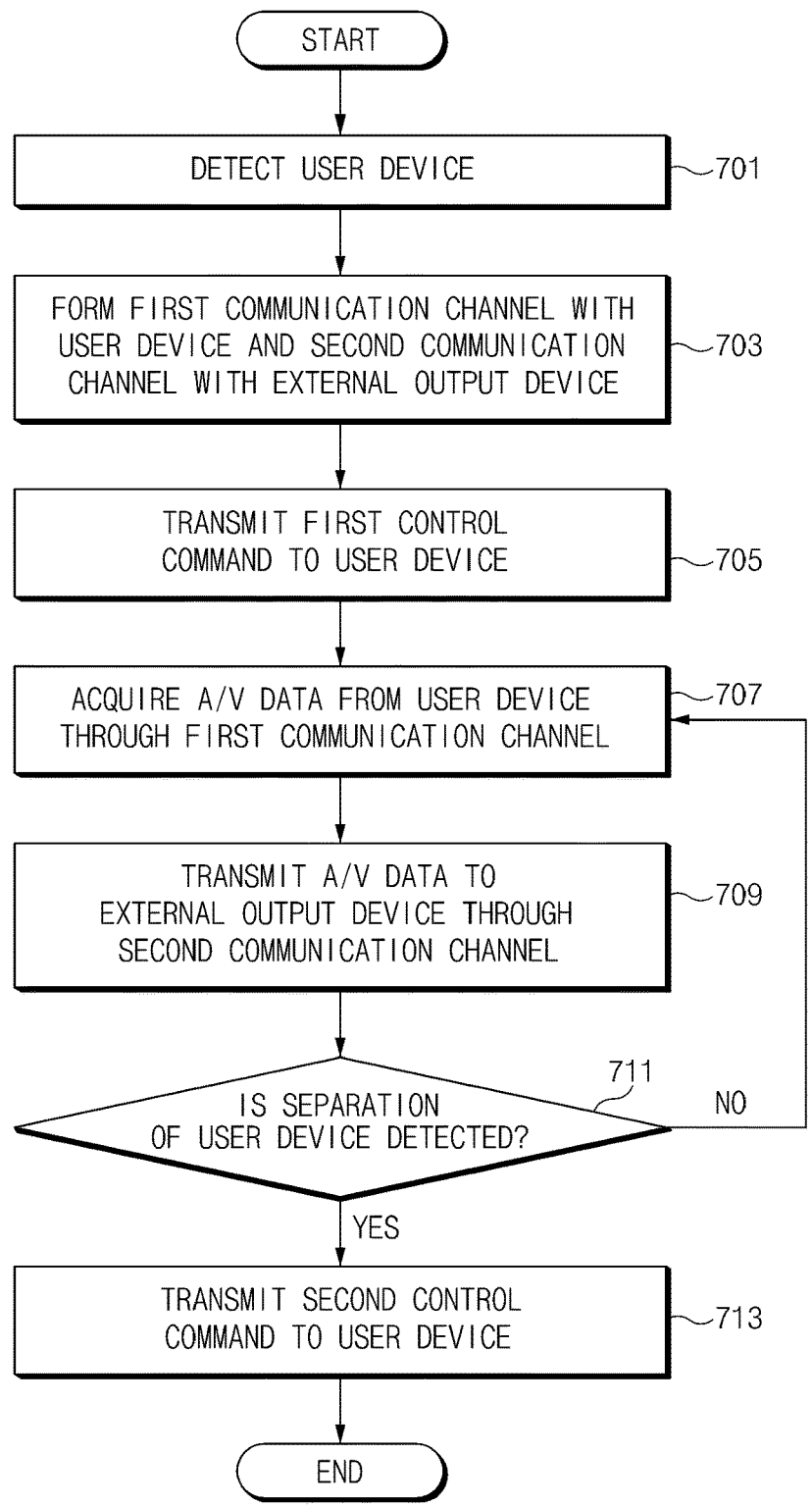
FIG. 7 is a flowchart of a method of performing media plugging by a control station, according to an embodiment of the present disclosure.

FIG. 7 is a flowchart of a method of performing media plugging by a smart station, according to an embodiment of the present disclosure.

Referring to FIG. 7, in operation 701, the smart station 100 may detect whether the user device 240 is positioned on a planar surface of the smart station 100. For example, the (pressure) sensor 120 included under the planar surface of the smart station 100 detects a pressure of a specific value or higher, the smart station 100 may determine that the user device 240 is located on the smart station 100.

If the user device 240 is detected, in operation 703, the smart station 100 may form a first communication channel with the user device 240 and may form a second communication channel with an external output device. Here, the external output device may include a video output device, such as the informative mirror display 210 or the modular display 230, and/or an audio output device such as the speaker 220.

The first communication channel may correspond to a communication channel using short range communication such as Bluetooth. Further, the second communication channel may correspond to a channel using wireless communication, such as Wi-Fi. For example, the in-room devices in the room 20 service environment may be connected with each other on one Wi-Fi network. The smart station 100 may function as an access point (AP) of the Wi-Fi network.

In operation 705, the smart station 100 may transmit a first control command to the user device 230. The first control command may be a command to transmit content, which is being currently output by the user device 240, to the smart station 100. Here, the content, which is being output by the user device 200, may correspond to an image that is being displayed on the user device 240, or a video that is being reproduced by the user device 240.

The user may position the user device 240 on the smart station 100 while the display of the user device 240 is turned off or a separate application is not being executed, and in this instance, the smart station 100 may receive a message that says that no content is being currently output, in response to a first control command. However, because this context is meaningless in a media plugging scenario, it is assumed in FIG. 7 that the user device 240 is executing an arbitrary audio/video (A/V).

The first control command may include a command to cease or terminate output of the user device 240, in addition to a command to transmit content, which is being output, that is, the A/V data of the content to the smart station 100.

For example, if audio and video outputs of the user device 240 are ceased and the display of the user device 240 is switched off while the content is output by an external output device, audio disturbances by two output devices (the speaker of the user device 240 and the external speaker 220) may be prevented while consumption of the battery is reduced.

In operation 707, the smart station 100 may obtain A/V data from the user device 240 through the first communication channel. In operation 709, the smart station 100 may transmit the obtained A/V data to an external output device, through the second communication channel.

The external output device, which has received the A/V data from the smart station 100, may output the received A/V data. For example, if the user device 240, which is reproducing music, is positioned on the smart station 100, the smart station 100 may cease output of the user device 240 and allow the horn speaker 220 to output audio data. Further, if the user device 240, which is reproducing a movie or a drama, is positioned on the smart station 100, the smart station 100 may cease video/audio outputs of the user device 240 and allow the informative mirror display 210 to output the movie or drama. While the media of the user device 240 is being reproduced through another output device, the user device 240 may charge the battery through wireless charging from the smart station 100.

The smart station 100 may turn off only an audio output of the user device 240. For example, the user may feel like continuously controlling the screen of the user device 240 while listening to the music through the horn speaker 220. The smart station 100 may output the screen output on the user device 240, on the informative mirror display 210, without turning off the display of the user device 100. For example, when the user processes a slide show such as PPT, the user may output the PPT slide on the informative mirror display 210 such that other people may watch the PPT slide and may directly perform control of pages, or the like.

The user device 240 may be separated from the smart station 100. For example, in operation 711, the smart station 100 may detect that the user device 240 is no longer positioned on the smart station 100, based on a change of a sensed value of the pressure sensor or the like. In this instance, in operation 713, the smart station 100 may transmit a second control command to the user device 240. Here, the second control command may be a command to cause the user device 240 not to transmit A/V data to the smart station 100. If a response to the second control command is received, the smart station 100 may release the first communication channel formed between the smart station 100 and the user device 240. However, if separation of the user device 240 is detected, the smart station 100 may cease transmission of data of the user device 240 by releasing the first communication channel, without transmitting the second control command.

Figure 8:
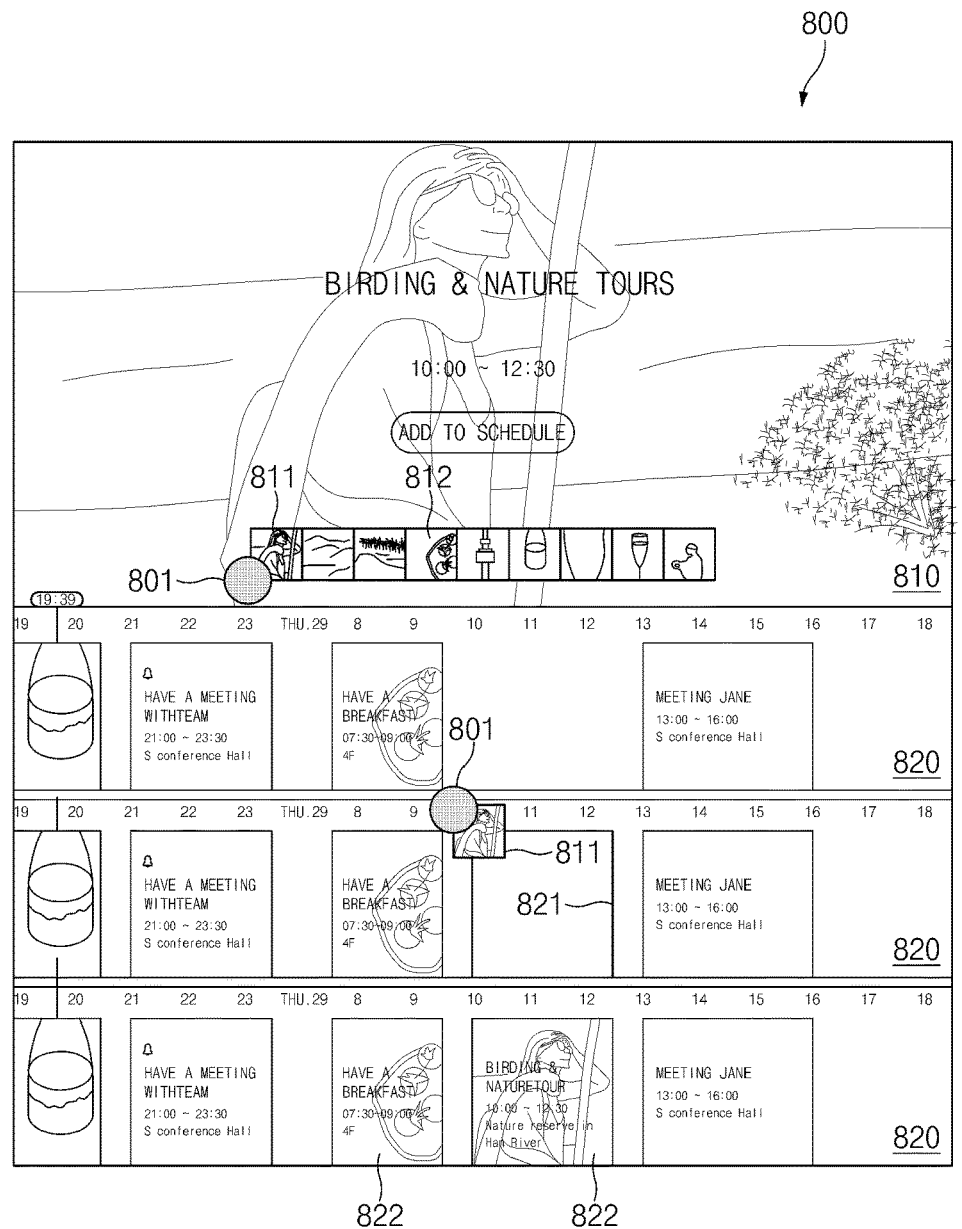
FIG. 8 is a diagram of a schedule providing scenario, according to an embodiment of the present disclosure.

FIG. 8 is a diagram of a schedule providing scenario (e.g., Timely Info), according to an embodiment of the present disclosure.

A schedule suggesting screen 800 may be output from at least one of the informative mirror display 210, the modular display 230, or the tablet 250. For example, the smart station 100 may fetch a hotel schedule that includes a plurality of programs provided by the hotel 30, from the hotel system 31. For example, the smart station 100 may fetch information on business hours of a breakfast/lunch/dinner providing restaurant of the hotel, activities recommended by the hotel, or a regular seminar or program of the hotel 30, from the hotel system 31. Further, the smart station 100 may obtain user information, such as preferred foods or preferred activities of the user, which have been registered when the user checked into the hotel 30 or has been constructed in a database in advance through an application, from the hotel system 31.

The smart station 100 may obtain a schedule of the user, from the user device. Based on the obtained information, the smart station 100 may constitute the schedule suggesting screen 800 and output the schedule suggesting screen 800 on the informative mirror display 210 or the like.

In the embodiment of FIG. 8, the smart station 100 may be replaced by the hotel control system 21.

The schedule suggesting screen 800 includes a first area 810 that displays information on a currently selected program of a plurality of programs provided by the hotel 30, and a second area(s) 820 that displays a time table reconstructed based on the schedule of the user. For example, the first area 810 may provide the plurality of programs provided by the hotel 30 in a form of an icon or a list. When the current schedule of the user is considered, a first available program 811 and a second unavailable program 812 may be included in the first area 810. The first program 811 and the second program 812 may be displayed differently, based on the schedule and/or user information of the user. For example, in the schedule of the user registered in advance in the corresponding time slot, the second unavailable program 812 may be displayed in a black and white thumbnail, and the first available first program 811 may be displayed in a color thumbnail.

If a user input 801 for selecting the first program 811 is made in the first area 810, a time section corresponding to the first program 811, that is, a slot 821 that corresponds to 10:00 to 12:30 may be displayed in the second area 820 in a specific manner (e.g., a solid line). If the user input 801 drags a thumbnail of the first program 811 and drops the dragged thumbnail in the slot 821, the first program 811 may be added to the schedule of the user. The smart station 100 may transmit information that the first program 811 has been added to the schedule of the user, to the hotel system 31, and the hotel system 31 may allow a department that is responsible for the first program 811 to identify (e.g., make a phone call or transmit a message to the user device 240) whether the user actually uses the first program 811 and provide suitable information.

In the embodiment of FIG. 8, in the time slot of 07:30 to 09:30, a breakfast (e.g., a first restaurant) is registered in advance as a schedule. However, if the user drags and drops another schedule (e.g., a second restaurant), at least a portion of which overlaps the corresponding time slot similarly to the above-described first program 811, the user device 240 may register a breakfast in a second restaurant as a new schedule, and may cancel the overlapping schedule, that is, the breakfast in the first restaurant. In this instance, the smart station 100 may transmit information on the changed schedule to the hotel system 31, and the hotel system 31 may provide the changed reservation information to the restaurants.

Figure 9:
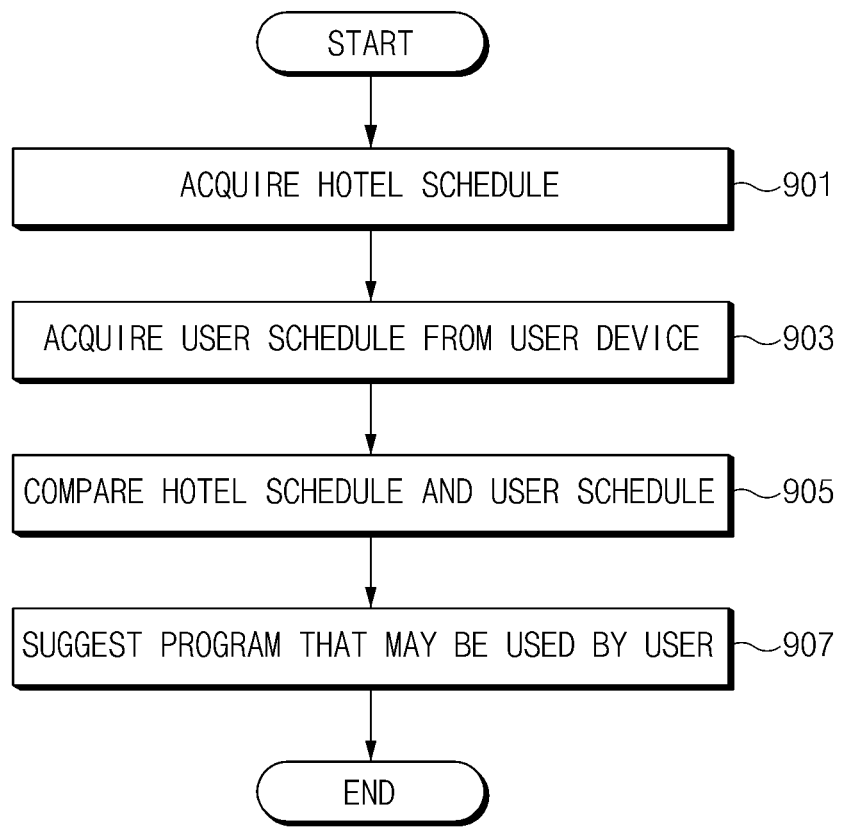
FIG. 9 is a flowchart of a method of performing a schedule providing scenario by a control station, according to an embodiment of the present disclosure.

FIG. 9 is a flowchart of a method of performing a schedule providing scenario by a smart station, according to an embodiment of the present disclosure.

The method of FIG. 9 may be performed by the smart system 100, or may be performed by the room control system 21 or the hotel system 31. Hereinafter, for sake of convenience, it will be described that the smart station 100 performs the method of FIG. 9. The smart station 100 may use the informative mirror display 210, the modular display 230, the tablet 250, or the like, which is connected with the smart station 100 through a network, to provide a UI, for example, such as the schedule suggesting screen 800 of FIG. 8. However, the method of FIG. 9 may be performed by a hotel application installed in the user device 240.

For example, the smart station 100 may fetch a hotel schedule that includes a plurality of programs provided by the hotel 30, from the hotel system 21. The smart station 100 may obtain user information registered when the user checked into the hotel 30 or constructed in a database, together with the hotel schedule, from the hotel system 21.

In operation 902, the smart station 100 may obtain a user schedule registered in the user device 240 of the user, from the user device 240. For example, the smart station 100 may fetch a schedule registered for a period (dates) for which the user stays in the hotel 30, from a schedule management application or a calendar application of the user, an outlook application, or the like. The smart station 100 may obtain schedule information of the user, and then may obtain an authority that is necessary for reflecting schedule information added or removed through a user interaction on the user device in a process of registering the user device 240 when the user checks into the hotel 30.

In operation 905, the smart station 100 may compare a hotel schedule with a user schedule. For example, in the example of FIG. 8, the smart station 100 may identify that a schedule of the user is empty for times slots of 09:30 to 13:00 and after 06:00 on the 29th. The smart station 100 may identify a program, which may be used by the user, of a plurality of programs. For example, the smart station 100 may determine a first program 811 (e.g., BIRDING & NATURE TOURS), which is progressed from 10:00 to 12:00 on the 29th, as an available program.

In operation 907, the smart station 100 may suggest the determined program. For example, the smart station 100 may distinguish (e.g., a color/black and white icon) a program item that may be used by the user from a program item that cannot be used by the user, according to a preset schedule of the user, on a UI such as the schedule suggesting screen 800, to provide the distinguished program items.

For example, as in the method of FIG. 8, if the suggestion is accepted, the smart station 100 may register a schedule for the suggested program in the user device 240, and may provide information that indicates that the user has applied for the suggested program in the hotel system 31.

Figure 10:
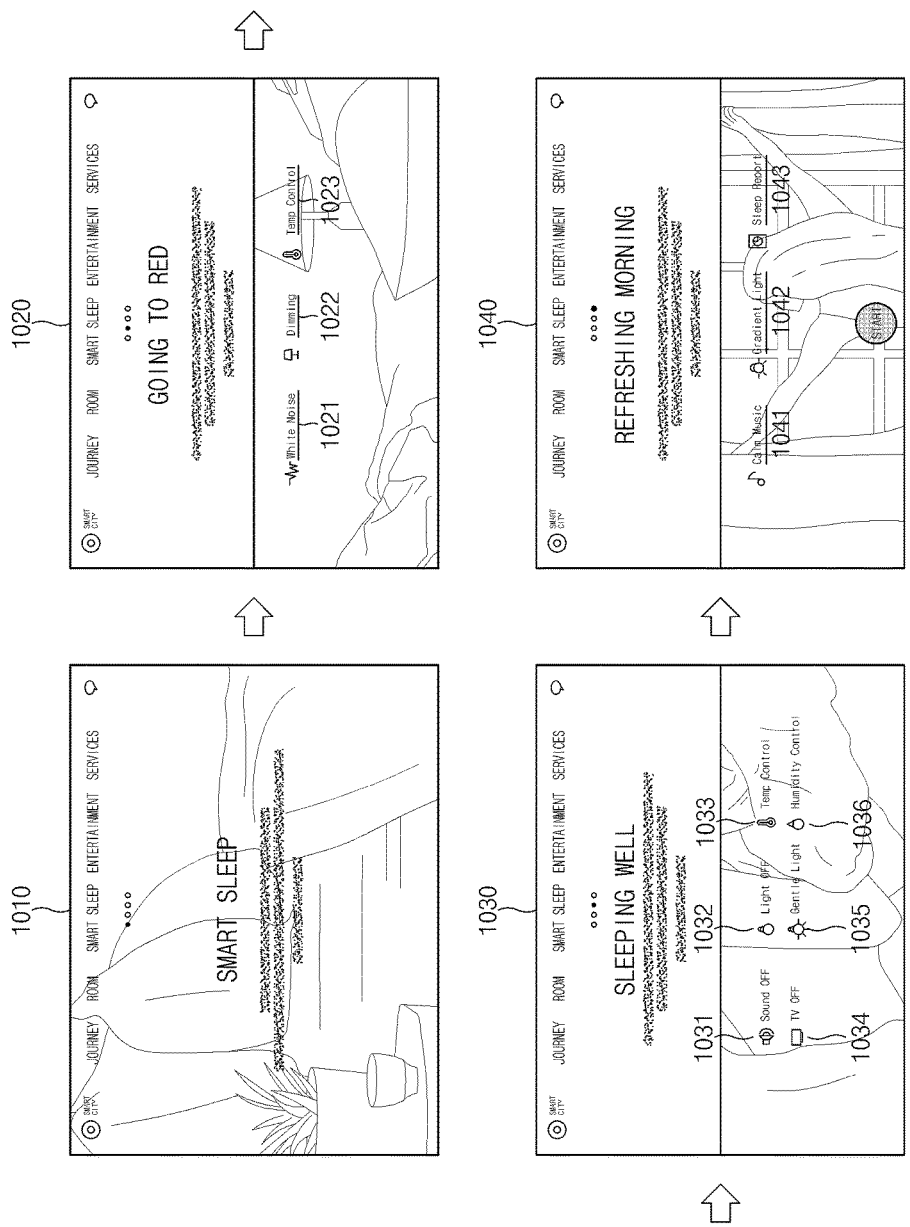
FIG. 10 is a diagram illustrating how to set a smart sleep, according to an embodiment of the present disclosure.

FIG. 10 is a diagram illustrating how to set up a smart sleep, according to an embodiment of the present disclosure.

The UIs of FIG. 10 may be provided through the informative mirror display 210 or the tablet 250. For example, information that indicates that the user is about to sleep (e.g., turns off light and is laid on the bed) is received from a sleep sensor 261 attached to the bed in the room, the smart station 210 may allow the information mirror display 210 or the tablet 250, or both of them to output an information screen 1010 of the smart sleep service.

If a touch input (e.g., a left drag) is made to the information screen by the user, the tablet 250 may display a first setting screen 1020 corresponding to the touch input. The first setting screen 1020 may display settings that are provided in a step of preparing a sleep by the user. For example, items on white noise 1021, dimming 1022, and a temperature control 1023 may be displayed. The user may select an arbitrary item of the items displayed on the first setting screen 1020 to turn on or off the corresponding function or adjust values. For example, a user who prefers no light may select a dimming 1022 item to turn off the dimming 1022 function before sleeping.

If the setting of the first setting screen 1020 is finished, the user may proceed to a second setting screen 1030 through a touch input. The second setting screen 1030 may display settings that will be applied after it is identified that the user is sleeping. For example, items such as sound off 1031, light off 1032, a temperature control 1033, TV off 1034, soft light 1035, and a moisture control 1036 may be displayed. The user may select an arbitrary item of the items displayed on the second setting screen 1030 to turn on or off the corresponding function or adjust values. For example, the user prefers to fall asleep while watching TV, he or she may select the TV off 1034 function to set the TV such that the TV is turned off 15 minutes after he or she falls asleep. In this instance, if is determined that the user is sleeping based on information collected from various sensors (e.g., a snoring sound or a tossing and turning sound), the smart station 100 may turn off the TV function of the informative mirror display 210 15 minutes after the determination time point.

If the setting of the second setting screen 1030 is finished, the user may proceed to a third setting screen 1040 through a touch input. The third setting screen 1040 may display settings that will be applied when the user wakes up. For example, items including calm music 1041, gradient light 1032, and a sleep report 1043 may be displayed. The user may select an arbitrary item of the items displayed on the third setting screen 1040 to turn on or off the corresponding function or adjust values. For example, the user may change music that will be provided at a wakeup time point by selecting the calm music 1041 item, or may change the volume of the music.

The setting value changed by the user may be delivered to the smart station 100 (or the room control system 21) through a wireless network. The smart station 100 may transmit a control command defined through settings, to a lighting device, an audio output device (e.g., the speaker 220), a video output device (e.g., the informative mirror display 210), a moisture controller, a ventilation system, a cooling/heating system, and the like, based on a sleeping state (preparing to sleep, sleeping, or waking up) of the user.

Figure 11:
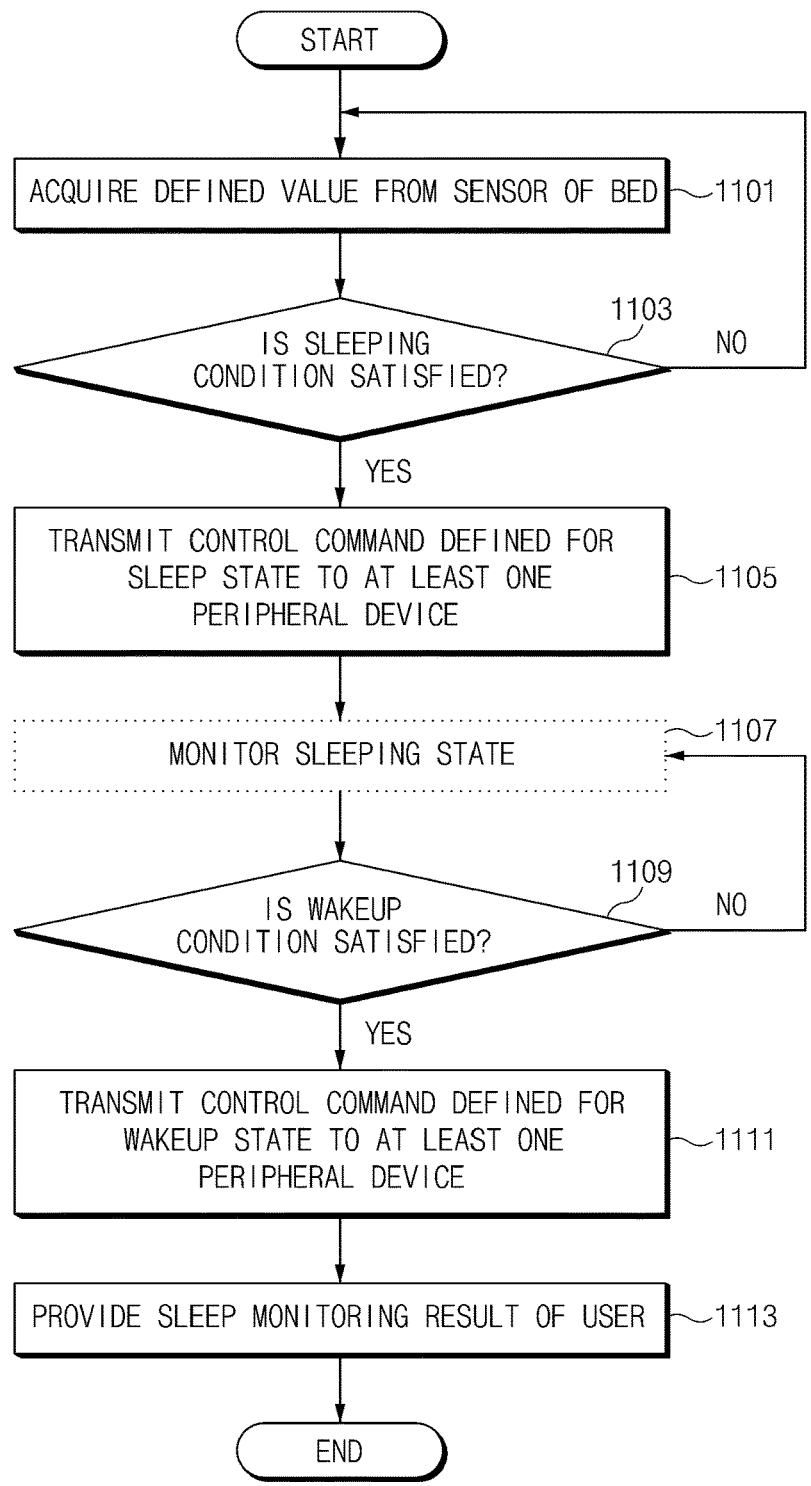
FIG. 11 is a flowchart of a method of performing a smart sleep by a control station, according to an embodiment of the present disclosure.

FIG. 11 is a flowchart of a method of performing a smart sleep scenario by a smart station, according to an embodiment of the present disclosure.

In operation 1101, the smart station 100 may obtain a defined value from the sleep sensor 261 of the bed. For example, the sleep sensor 261 attached to the bed may detect different pressures when the user is seated and laid on the bed. The sleep sensor 261 may transmit a predefined value (e.g., 1) to the smart station 100 if a pressure corresponding to the case in which the user is laid is detected, and may transmit another predefined value (e.g., 0) if it is determined that a pressure is detected but the user is not laying down. When a pressure is not detected, the sleep sensor 261 may not transmit data. However, the smart station 100 may directly receive an input value from the sleep sensor 261.

In operation 1103, the control circuit 110 of the smart station 100 may determine whether a sleeping condition is satisfied. For example, the control circuit 110 may determine whether the sleeping condition is satisfied based on a value received from the sleep sensor 261, a current time, a schedule of the user, values collected from other sensors, such as the luminance sensor 267. For example, the control circuit 110 may determine whether the state associated with the sleep of the user corresponds to a sleep preparing state, a sleeping state, or a wakeup state.

In operation 1105, the control circuit 110 may transmit predefined control commands for the states associated with the sleep, to the in-room devices connected with the network, through the communication circuit 140. For example, the control circuit 110 may transmit control commands that are defined differently based on whether the user is preparing for sleep, is sleeping, or is in a wakeup state, to the in-room devices. The control commands, for example, may be defined based on the user settings described with reference to FIG. 10. When the user has visited the hotel before and has set the smart sleep one or more times, the last setting value may be basically defined. The smart circuit 110 may transmit a suitable control command to the lighting device, the audio output device, and the video output device placed in the room. For example, a command to completely turn off lighting may be transmitted to the lighting device, a command to output white noise may be transmitted to the horn speaker 220, and a command to cease output of the TV may be transmitted to the informative mirror display 210 after a specific time period.

In operation 1107, the control circuit 110 may monitor a sleeping state of the user by using the sensors included in the room. This operation may be excluded based on a selection of the user. When the user turns off a function 1043 of report a sleep in the third setting screen 1040, the monitoring of the sleeping state of the user may not be performed.

In operation 1109, the control circuit 110 may determine whether a wakeup condition is satisfied. If not satisfied, the control circuit 110 may continuously perform the monitoring or wait until the wakeup condition is satisfied. If the wakeup condition is satisfied, the control circuit 110 may perform operation 1111.

In operation 1111, the control circuit 110 may provide a command that is defined for the wakeup state, to the peripheral devices. For example, the control circuit 110 may transmit a command to output calm music to the audio output device 220, and a command to generate gentle lighting to the lighting device, based on the information set by the third setting screen 1040.

In operation 1113, the control circuit 110 may provide a result obtained by monitoring a sleeping state of the user. For example, the control circuit 110 may provide the collected monitoring result to a display device, such as the tablet 250 or the informative mirror display 210, and allow the corresponding display device to provide information on the sleeping state of the user.

Figure 12:
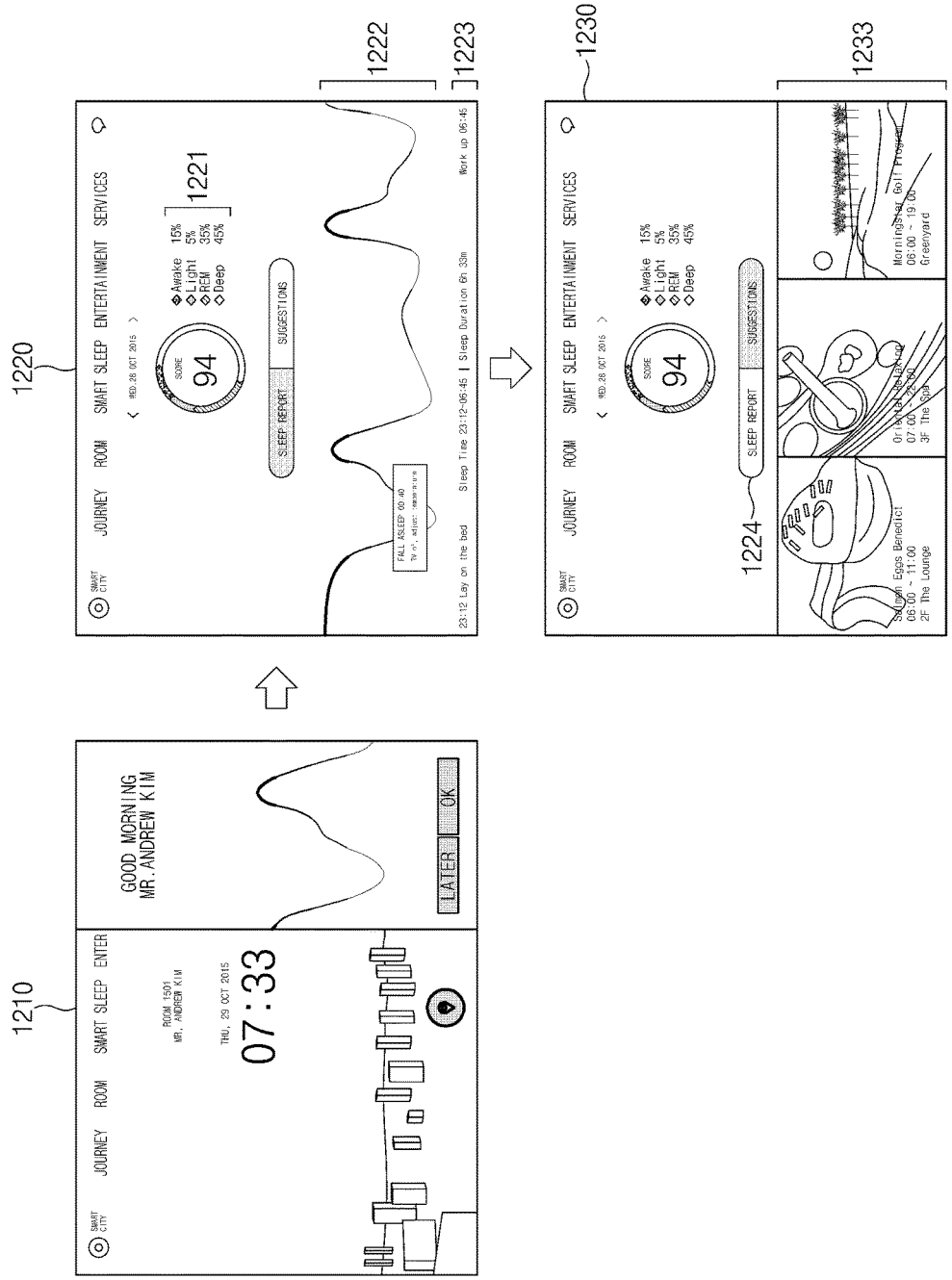
FIG. 12 is a diagram illustrating how to provide an analysis result of a smart sleep, according to an embodiment of the present disclosure.

FIG. 12 is a diagram illustrating how to provide an analysis result of a smart sleep, according to an embodiment of the present disclosure.

A first screen 1210 illustrates a screen that is provided to the informative mirror display 210 or the tablet 250 when the user wakes up. A portion of information (e.g., a graph) that indicates a current time and a sleeping state of the user may be displayed on the first screen 2010.

The user may identify information on the sleeping state from the second screen 1220. For example, value (e.g., ratios or scores) data 1221 and a sleep graph 1222 for time slots based on a depth of the sleep (e.g., an awake sleep, a light non-REM sleep, a deep non-REM sleep, or a REM sleep) of the user. Further, time information 1223 that indicates a time when the user is laying in the bed, a time when the user falls asleep, a sleep duration, or a wakeup time may be included in the second screen 1220.

The user may select a suggestion menu 1225 from the second screen 1220 and identify programs 1233 associated with the sleep state or the wakeup time. In this state, if the sleep report 1224 menu is selected again, the screen may return to the second screen 1220.

Figure 13:
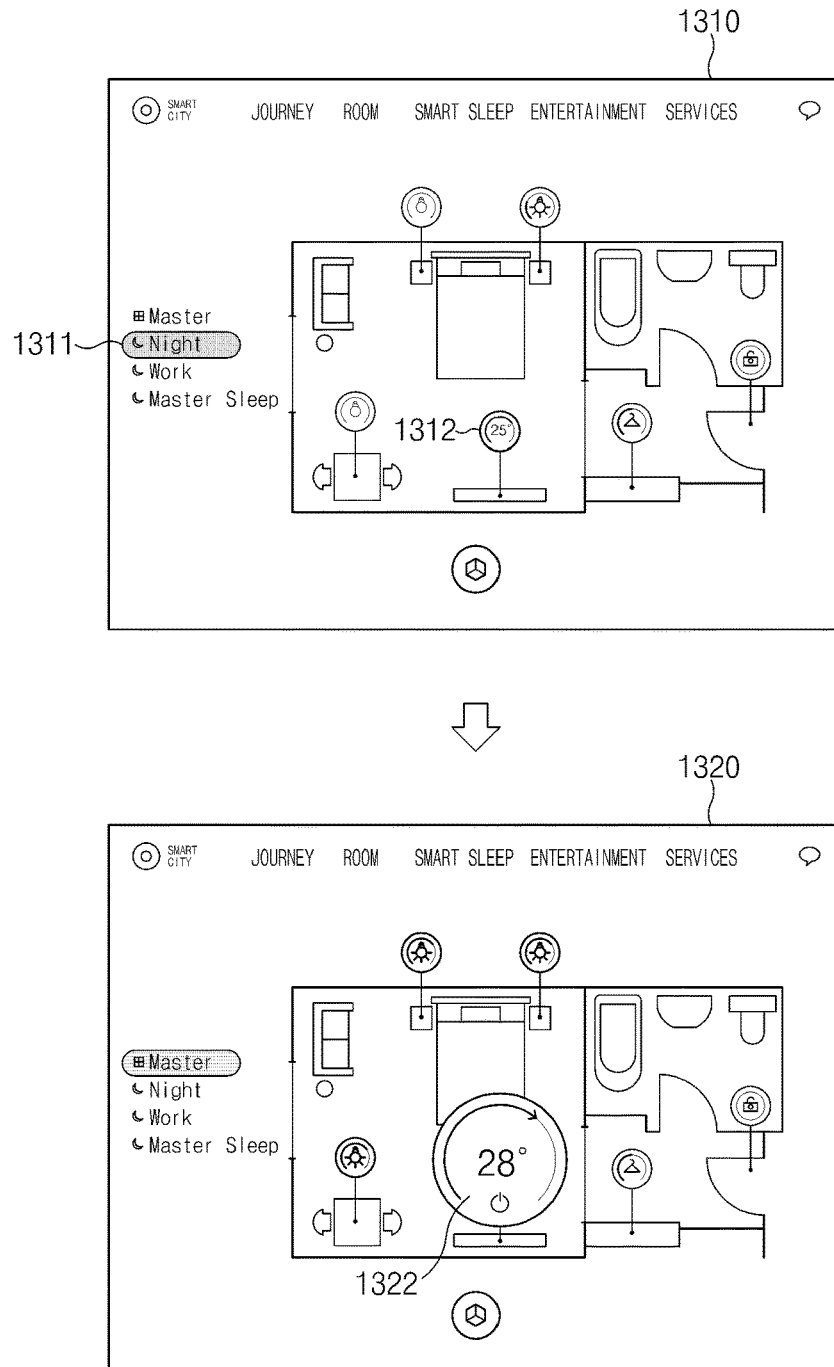
FIG. 13 is a diagram illustrating how to control in-room devices, according to an embodiment of the present disclosure.

FIG. 13 is a diagram illustrating how to control in-room devices, according to an embodiment of the present disclosure.

The screens of FIG. 13 may be screens for recognizing the whole room 20 at one time through the tablet 250 or the like and controlling the devices placed in the room 20 or the room environment.

For example, the tablet 250 may output a specific screen on the display, based on a user input. For example, detailed information on a plurality of items arranged in the room 20 may be stored in a memory of the tablet 250. Here, the plurality of items may correspond to a plurality of devices, of which an operation state (e.g., ON/OFF) may be changed by a user input for an item output on the display of the tablet 250 or of which a setting value (e.g., temperature or humidity of the interior of the room) may be changed. For example, a drawing that illustrates equipment or electric products in the room 20, or arrangement of facilities and a plurality of items that may be controlled in the drawings may be displayed on the first screen 1310. If a temperature item 1312 is selected by the user, a screen displayed on the display of the tablet 250 (e.g., a processor included in the tablet 250) may be switched to a second screen 1320. The selected temperature item 1312 may be displayed as an expanded temperature item 1322 in the second screen 1320. The expanded temperature item 1322 may include a value (e.g., 28 degrees) set through a user input, a current temperature, or a temperature (e.g., 25 degrees) that has been set before the user input. If the setting value is changed, the tablet 250 may transmit the changed information to the smart station 100 and/or the room control system 21. The smart station 100 and/or the room control system 21 may control the devices related, for example, to the temperature, the moisture, and lighting of the room, based on the changed room setting.

Figure 14:
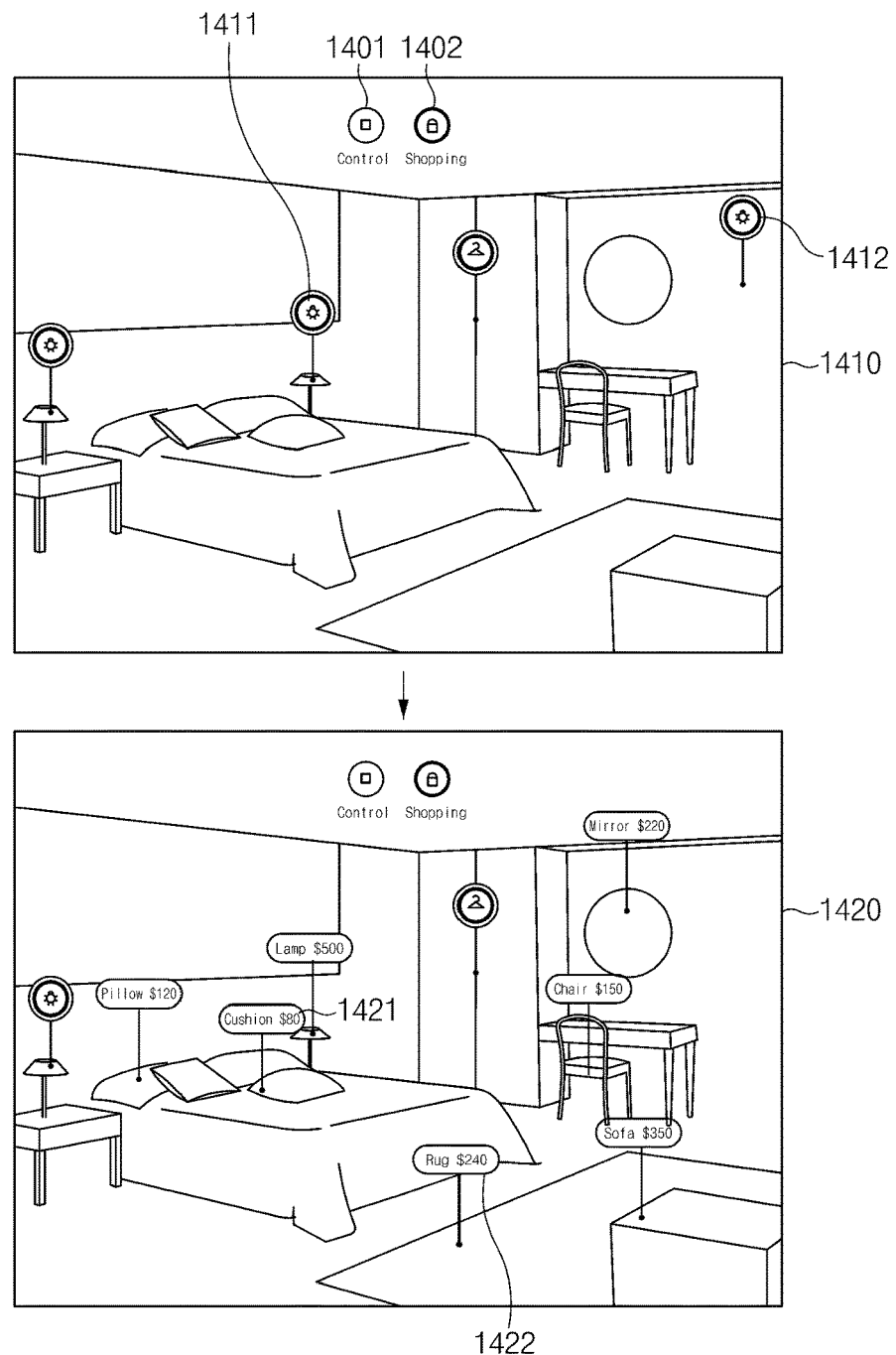
FIG. 14 is a diagram illustrating how to control in-room devices and provide information related to a room, according to an embodiment of the present disclosure.

FIG. 14 is a diagram illustrating how to control in-room devices and provide information related to a room, according to an embodiment of the present disclosure.

Referring to FIG. 14, an image of the interior of the room 20 obtained by a camera module of the tablet 250 may be output on the display of the tablet 250. In this instance, detailed information on the in-room devices that are predefined as being arranged in the space of the room may be stored in the memory of the tablet 250. Here, the detailed information may include images of the in-room devices, which have been captured in advance. If an image captured by the camera module matches with an image of an in-room device that has been stored in advance, the tablet 250 may output a control item for controlling the corresponding in-room device above the corresponding image. For example, because the location of a light bulb in the room is located at a fixed location with respect to the structure of the room and the main furniture arranged in the room, the tablet 250 may recognize a light bulb mapped with the image obtained by the camera module. If mood lights arranged on the left and right sides of the bed is recognized from the image 1410 obtained by the camera module, a control item 1411 corresponding to the mood lights may be displayed. The user may select the control item, and may turn on or off the mood lights or adjust the brightness of the mood lights. Further, the light bulb arranged on a wall surface is recognized, a control item 1412 corresponding to the light bulb may be displayed, and the user may also turn on or off the light bulb by selecting the control item 1412. Although a conventional hotel room is equipped with a plurality of light bulbs and a user who stays in the room for a relatively short period, e.g., two or three days, cannot easily find switches for controlling the light bulbs, according to an embodiment of the present disclosure, the user can easily control the in-room devices.

If a shopping menu 1402 is selected, the tablet 250 may output an image 1420 on the display. If an image captured by a camera matches with an image of a room article, which is stored in advance, the purchase price of the room article may be output above the corresponding image. For example, the price corresponding to an image 1412 of a cushion may be displayed as $80. In this way, the user may easily identify information on an item, which may be purchased, of the items placed in the room 20. If a control menu 1401 is selected, the tablet 250 may output the image 1410 on the display.

Figure 15:
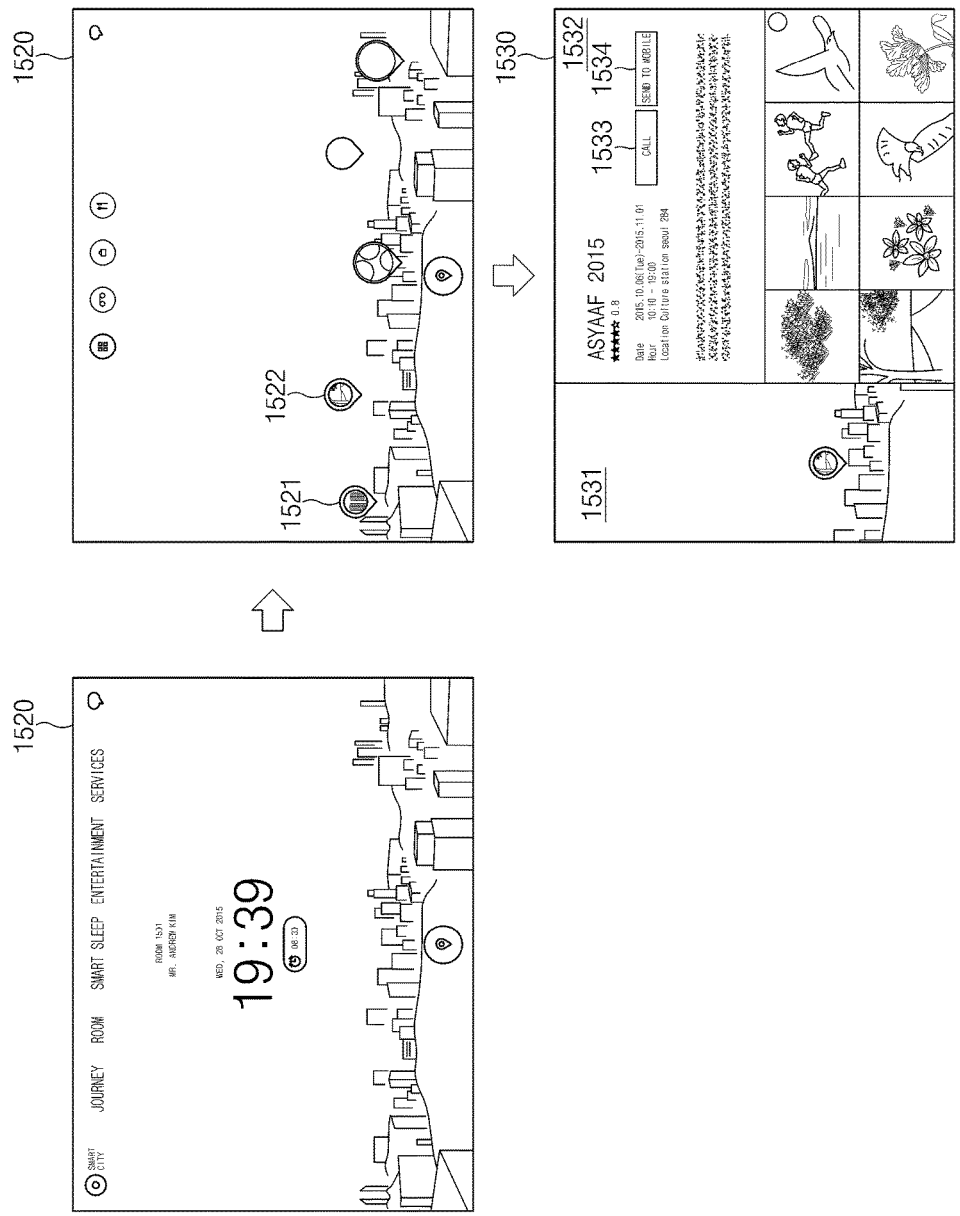
FIG. 15 is a diagram illustrating how to provide an analysis result of a smart sleep, according to an embodiment of the present disclosure.

FIG. 15 is a diagram on how to provide an analysis result of a smart sleep, according to an embodiment of the present disclosure.

The user may view the outside of a glass window of the room 20 while carrying the tablet 250 placed in the room. The tablet 250 may include a position sensor (e.g., a GPS), a geomagnetic sensor, and a gyro sensor, and may determine a direction which the tablet 250 is currently facing, based on the location of the room and the direction of the magnetic field of the earth.

If the direction which the tablet is currently facing is determined, the tablet 250 may output an image 1510 of a scene, which is viewed by the user when the user views the direction from the room, on the display. For example, a night scene image around the room or a scene image in a suitable time slot may be stored in the tablet 250, and at least an area of the image may be displayed based on the determined direction.

The table 250 may display information on tour sites, restaurants, events, or landmarks, on the scene image 1510. For example, the table 250 may display an icon regarding a place, of which information has been registered in advance, of the scene images in a first screen 1520. For example, an item corresponding to COEX 1512 (Convention & Exhibition Center) or ASYAAF (Asian Students and Young Artists Art Festival) 1522 may be displayed.

If any one of the displayed items is selected, the tablet 250 may display a second screen 1530. If it is assumed that ASYAAF 1522 is selected, the second screen 1530 may include a first area 1531 that has a specific transverse width with respect to ASYAAF 1522, which has been selected from the scene images output from the first screen 1520, and a second area 1532 that includes detailed information on ASYAAF 1522. The second area 1532 may include information on ASYAAF registered in the hotel system 31 and related menus, e.g., a phone call menu 1533 or an information transmission menu 1534 to transmit information of ASYAAF to the user device 240. In order to provide information on, for example, an event or a festival, which may be provided for the length of stay of the user, the tablet 250 may receive information, which will be output on the first screen 1520 and the second screen 1530, from the hotel system 31 or the room control system 21 through a wireless network.

Figure 16:
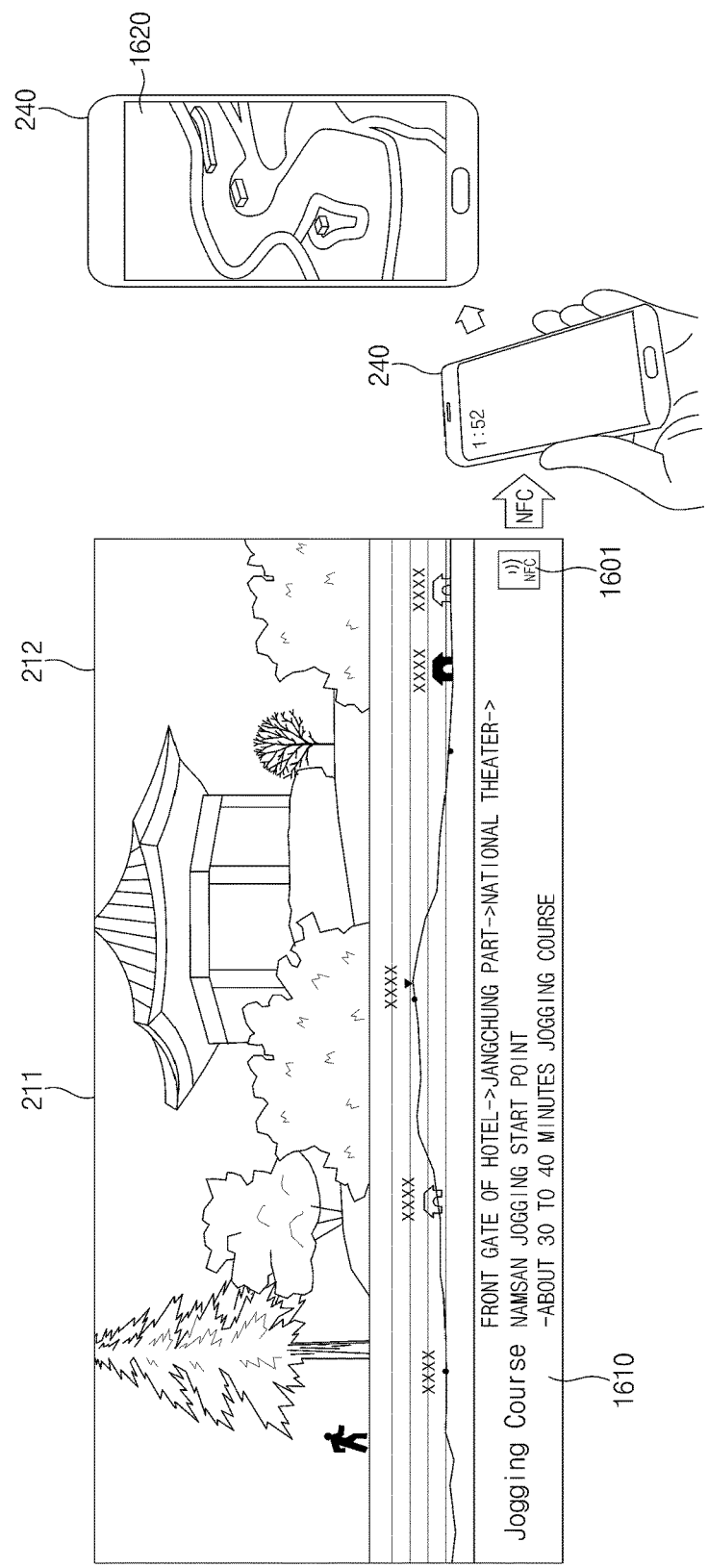
FIG. 16 is a diagram illustrating how to fetch information provided by the hotel to the user device, according to an embodiment of the present disclosure.

FIG. 16 is a diagram illustrating how to fetch information provided by the hotel to the user device, according to an embodiment of the present disclosure.

Referring to FIG. 16, information 1610 on a jogging course may be provided on the informative mirror display 210 as a program provided by the hotel. The information 1610 on the jogging course may be displayed throughout the first display device 211 and the second display device 212.

The second display device 212, for example, may be equipped with an NFC function, as in the display device 420 of FIG. 4. In this instance, an icon 1601 that indicates that NFC tagging is supported may be displayed on the second display device 212.

When the user device 240 supports an NFC function, the user also may allow the user device 240 to approach an NFC icon 1601 to perform the NFC communication. In this instance, the second display device 212 may transmit information, which is being currently output on the informative mirror display 210, to the user device 240. The second display device 212 may transmit information 1620 on a jogging course, which has been adjusted based on a resolution of the user device 240, to the user device. If the second display device 212 delivers information that NFC tagging of the user device 240 is generated for a jogging course program, which is being output, to the smart station 100 or the room control system 21, the smart station 100 may transmit the information 1620 on the adjusted jogging course to the user device 240 through a wireless network. However, the second display device 212 may directly establish a communication channel with the user device 240 and may transmit the information 1620 on the jogging course, for example, through a Bluetooth channel.

Each of the elements described in the specification may include one or more components, and the terms of the elements may be changed according to a type of the electronic device. The electronic device described herein may include at least one of the elements and some elements may be omitted or additional elements may be further included. Some of the elements of the electronic device may be coupled to form one entity, and may perform the same functions of the corresponding elements before they are coupled.

At least some of the devices (e.g., modules or functions) or methods (e.g., operations) described herein may be implemented by instructions stored in a non-transitory computer-readable storage medium, for example, in the form of a program module. When the instructions are executed by the control circuit 110, the control circuit 110 may perform a function corresponding to the instruction. The non-transitory computer-readable storage medium may be, for example, a memory 130.

The non-transitory computer-readable storage medium may include a hard disk, a floppy disk, a magnetic medium (e.g., a magnetic tape), an optical medium (e.g., a compact disk read only memory (CD-ROM)), a digital versatile disk (DVD), a magneto-optical medium (e.g., a floptical disk), and a hardware device (e.g., a read only memory (ROM), a random access memory (RAM), or a flash memory). Further, the program instructions may include high-level language codes which may be executed by a computer using an interpreter as well as machine languages created by using a compiler. The above-mentioned hardware device may be configured to be operated as one or more software module to perform operations of various embodiments, and the converse is true.

The module or program module described herein may include at least one of the above-mentioned elements, omit some of them, or further include other elements. The module, the program module, or the operations performed by other elements may be performed in a sequential, parallel, iterative, or heuristic method. Further, some operations may be executed in another sequence or may be omitted, or other operations may be added.

The devices placed in the room 20 may properly control contents based on a context, thereby further satisfying the user.

Further, programs that are provided by the hotel 30 may be intuitively provided based on the schedule of the user or the preference of the user.

Furthermore, the user may achieve a good night's rest while staying in the room 20 through management of a sleeping state of the user.

In addition, information on various products, events, tours, activities, or the like directly provided by the hotel 30 or associated with the hotel 30 may be provided to a user.

While the present disclosure has been shown and described with reference to certain embodiments thereof, it will be understood by those skilled in the art that various changes in form and details may be made therein without departing from the scope of the present disclosure. Therefore, the scope of the present disclosure should not be defined as being limited to the embodiments, but should be defined by the appended claims and equivalents thereof.

What is claimed is:

1. An electronic device comprising:
   a housing;
   a communication circuit configured to perform short range communication with a mobile device by using a first communication channel and perform wireless communication with an external output device by using a second communication channel; and
   a control circuit configured to:
   when the mobile device is located on or in close proximity to the housing, obtain, from the mobile device, a first schedule of a user registered in the mobile device through the first communication channel;
   perform a comparison of the first schedule of the user with a second schedule including programs;
   determine an available program from among the programs included in the second schedule based on the comparison; and
   transmit the available program to the external output device through the second communication channel.

2. The electronic device of claim 1, wherein the first communication channel corresponds to a Bluetooth communication channel and the second communication channel corresponds to a Wi-Fi communication channel.

3. The electronic device of claim 1, wherein the control circuit is configured to transmit to the mobile device a command signal to terminate at least one of audio and video outputs of the mobile device.

4. The electronic device of claim 1, further comprising:
   a pressure sensor configured to detect if the mobile device is positioned on the housing.

5. The electronic device of claim 4, wherein if a pressure obtained by the pressure sensor is greater than a threshold value, the control circuit determines that the mobile device is positioned on the housing, and if the pressure obtained is lower than the threshold value, the control circuit determines that the mobile device is not on the housing.

6. The electronic device of claim 5, wherein if it is determined that the mobile device is not on the housing, the control circuit transmits a command to terminate transmission of the content to the mobile device.

7. The electronic device of claim 5, wherein if it is determined that the mobile device is not on the housing, the control circuit releases the first communication channel established between the control circuit and the mobile device.

8. The electronic device of claim 1, further comprising:
a wireless charging circuit configured to supply electric power to the mobile device through the wireless charging circuit when the mobile device is placed on the housing.

9. The electronic device of claim 1, wherein the control circuit is further configured to generate a user interface including the available program and an unavailable program based on the comparison.

10. The electronic device of claim 9, wherein the available program and the unavailable program are visually differently presented in the user interface.

11. The electronic device of claim 1, wherein the control circuit is further configured to, in response to accepting the available program by the user, perform a registration of the available program to the first schedule of the user.

* * * * *